United States Patent
Griffin et al.

(10) Patent No.: US 12,245,758 B2
(45) Date of Patent: Mar. 11, 2025

(54) SELF-LOCKING TISSUE ANCHORS

(71) Applicant: 4Tech Inc., Edina, MN (US)

(72) Inventors: Patrick Griffin, Galway (IE); Ian O'Gorman, Galway (IE)

(73) Assignee: 4Tech Inc., Clayton, DE (US)

( * ) Notice: Subject to any disclaimer, the term of this patent is extended or adjusted under 35 U.S.C. 154(b) by 771 days.

(21) Appl. No.: 17/416,953

(22) PCT Filed: Dec. 20, 2019

(86) PCT No.: PCT/US2019/068009
§ 371 (c)(1),
(2) Date: Jun. 21, 2021

(87) PCT Pub. No.: WO2020/139776
PCT Pub. Date: Jul. 2, 2020

(65) Prior Publication Data
US 2022/0071616 A1    Mar. 10, 2022

Related U.S. Application Data

(60) Provisional application No. 62/784,670, filed on Dec. 24, 2018.

(51) Int. Cl.
*A61B 17/04* (2006.01)
*A61F 2/24* (2006.01)

(52) U.S. Cl.
CPC ............ *A61B 17/0401* (2013.01); *A61B 2017/0417* (2013.01); *A61B 2017/0464* (2013.01); *A61F 2/2457* (2013.01)

(58) Field of Classification Search
CPC .......... F16G 11/00; F16G 11/02; F16G 11/14; A61B 17/0401; A61B 2017/0417;
(Continued)

(56) References Cited

U.S. PATENT DOCUMENTS

| | | | | |
|---|---|---|---|---|
| 988,122 A | * | 3/1911 | McCarty | E06B 9/42 24/549 |
| 1,159,501 A | * | 11/1915 | Kimbark | F16B 45/012 24/698.3 |

(Continued)

FOREIGN PATENT DOCUMENTS

| CA | 2913610 A1 | 3/2005 |
|---|---|---|
| EP | 3284412 A1 | 2/2018 |

(Continued)

OTHER PUBLICATIONS

WIPO PCT Form ISA210, International Search Report for International Patent Application Serial No. PCT/US2019/068009 (Jul. 2, 2020).

(Continued)

*Primary Examiner* — Tan-Uyen T Ho
*Assistant Examiner* — Osama Nemer
(74) *Attorney, Agent, or Firm* — UltimatEdge IP Law Group, P.C.; Dean G. Stathakis

(57) ABSTRACT

A tissue anchor is provided that includes a metal wire shaped so as to define a straight anchor-shaft portion and a tissue-coupling portion extending therefrom. The tissue anchor is configured such that when the tissue-coupling portion is in an unconstrained state: (a) the tissue-coupling portion crosses itself at first and second loop-end longitudinal portions along the wire, so as to define a looped portion, which generally defines a looped-portion plane, (b) the first loop-end longitudinal portion is closer to a first proximal wire end along the wire than the second loop-end longitudinal portion is to the first proximal wire end along the wire, and (c) a greatest absolute distance between the first loop-end longitudinal portion and the first proximal wire end is greater than a greatest absolute distance between the second loop-end (Continued)

longitudinal portion and the first proximal wire end. Other embodiments are also described.

11 Claims, 11 Drawing Sheets

(58) Field of Classification Search
CPC .. A61B 2017/0464; A61B 2017/00243; A61B 2017/00845; A61F 2/2457; A61F 2/2442; A61F 2/2487
See application file for complete search history.

(56) References Cited

U.S. PATENT DOCUMENTS

| | | | | |
|---|---|---|---|---|
| 1,724,791 | A * | 8/1929 | Cain | B60D 1/187 24/129 C |
| 4,414,711 | A * | 11/1983 | Hubbard | F16G 11/143 24/131 R |
| 4,745,663 | A * | 5/1988 | Crowson | F16G 11/143 24/546 |
| 6,006,405 | A * | 12/1999 | Chou | F16G 11/046 24/131 R |
| 6,154,932 | A * | 12/2000 | Karg | F16G 11/046 24/131 R |
| 6,629,534 | B1 | 10/2003 | St. Goar et al. | |
| 6,743,198 | B1 | 6/2004 | Tihon | |
| 6,746,472 | B2 | 6/2004 | Frazier et al. | |
| 6,986,784 | B1 | 1/2006 | Weiser et al. | |
| 7,377,083 | B2 * | 5/2008 | McCafferty | E04C 5/163 52/712 |
| 8,323,316 | B2 * | 12/2012 | Maiorino | A61B 17/0401 606/228 |
| 8,398,672 | B2 * | 3/2013 | Kleshinski | A61F 2/0105 606/198 |
| 8,523,881 | B2 | 9/2013 | Cabiri et al. | |
| 8,641,704 | B2 | 2/2014 | Werneth et al. | |
| 9,186,152 | B2 | 11/2015 | Campbell et al. | |
| 9,510,833 | B2 | 12/2016 | Sato et al. | |
| 9,861,350 | B2 * | 1/2018 | Serina | A61B 5/686 |
| 10,071,243 | B2 | 9/2018 | Kuhn et al. | |
| 10,786,257 | B2 * | 9/2020 | Mathis | A61B 1/00085 |
| 2002/0013571 | A1 | 1/2002 | Goldfarb et al. | |
| 2003/0093096 | A1 * | 5/2003 | McGuckin, Jr. | A61B 17/0057 606/151 |
| 2004/0220596 | A1 | 11/2004 | Frazier et al. | |
| 2005/0251207 | A1 | 11/2005 | Flores et al. | |
| 2005/0273135 | A1 | 12/2005 | Chanduszko et al. | |
| 2005/0273138 | A1 | 12/2005 | To et al. | |
| 2006/0212047 | A1 | 9/2006 | Abbott et al. | |
| 2007/0010851 | A1 | 1/2007 | Chanduszko et al. | |
| 2007/0055333 | A1 | 3/2007 | Forde et al. | |
| 2007/0073337 | A1 | 3/2007 | Abbott et al. | |
| 2007/0250081 | A1 | 10/2007 | Cahill et al. | |
| 2008/0027446 | A1 | 1/2008 | Stone et al. | |
| 2009/0093670 | A1 | 4/2009 | Annest | |
| 2009/0112052 | A1 | 4/2009 | Lund et al. | |
| 2010/0312259 | A1 | 12/2010 | Houser et al. | |
| 2012/0179086 | A1 | 7/2012 | Shank et al. | |
| 2013/0232732 | A1 * | 9/2013 | Jacobson | F16G 11/143 24/265 H |
| 2013/0296925 | A1 | 11/2013 | Chanduszko et al. | |
| 2014/0275756 | A1 | 9/2014 | Bender et al. | |
| 2014/0275865 | A1 | 9/2014 | Taammam et al. | |
| 2014/0379074 | A1 | 12/2014 | Spence et al. | |
| 2015/0018940 | A1 | 1/2015 | Quill et al. | |
| 2015/0119920 | A1 * | 4/2015 | Mathis | A61B 17/12131 606/191 |
| 2017/0209137 | A1 * | 7/2017 | Gilmore | A61B 17/0057 |

FOREIGN PATENT DOCUMENTS

| | | |
|---|---|---|
| WO | 2004069055 A2 | 8/2004 |
| WO | 2015015497 A1 | 2/2015 |
| WO | 2016087934 A1 | 6/2016 |
| WO | 2016189391 A2 | 12/2016 |
| WO | 2018035378 A1 | 2/2018 |

OTHER PUBLICATIONS

WIPO, PCT Form ISA237, Written Opinion for International Patent Application Serial No. PCT/US2019/068009 (Jul. 2, 2020).
U.S. Appl. No. 15/104,467, filed Jun. 14, 2016, US 2017/0209137, U.S. Pat. No. 9,907,547.
U.S. Appl. No. 15/165,768, filed May 26, 2016, US 2016/0262741.
U.S. Appl. No. 15/619,881, filed Jun. 12, 2017, US 2017/0273681, U.S. Pat. No. 10,463,358.
U.S. Appl. No. 16/573,328, filed Sep. 17, 2019, US 2020/0022697, U.S. Pat. No. 10,588,618.
CNIPA Office Action for Chinese Patent Application Serial No. 2019800852002, pp. 16 (Feb. 29, 2024).
JPO Office Action for Japanese Patent Application Serial No. 536730/2021, pp. 5 (Sep. 12, 2023).

* cited by examiner

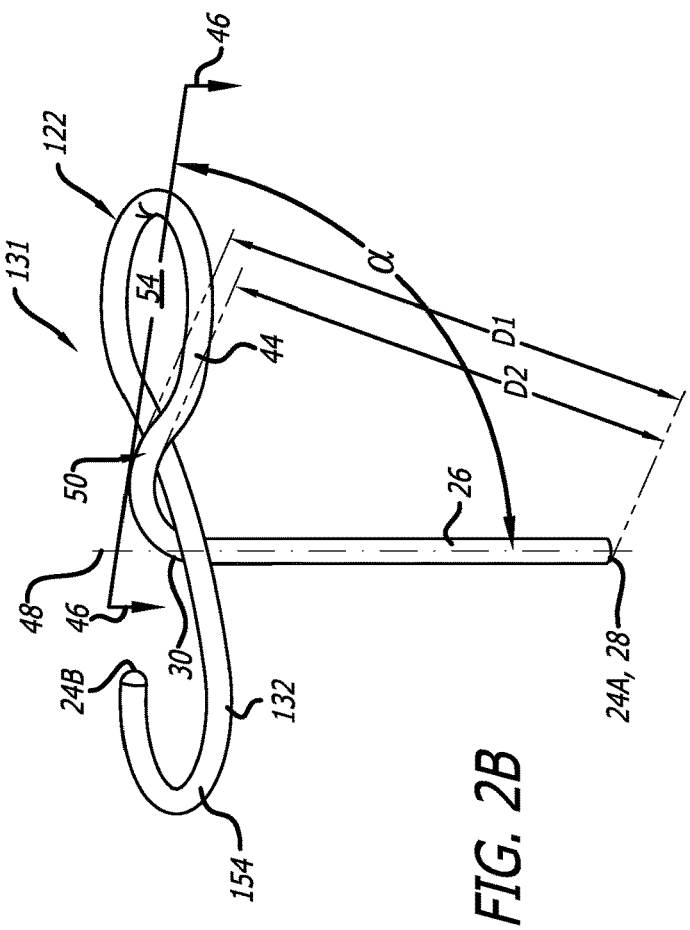
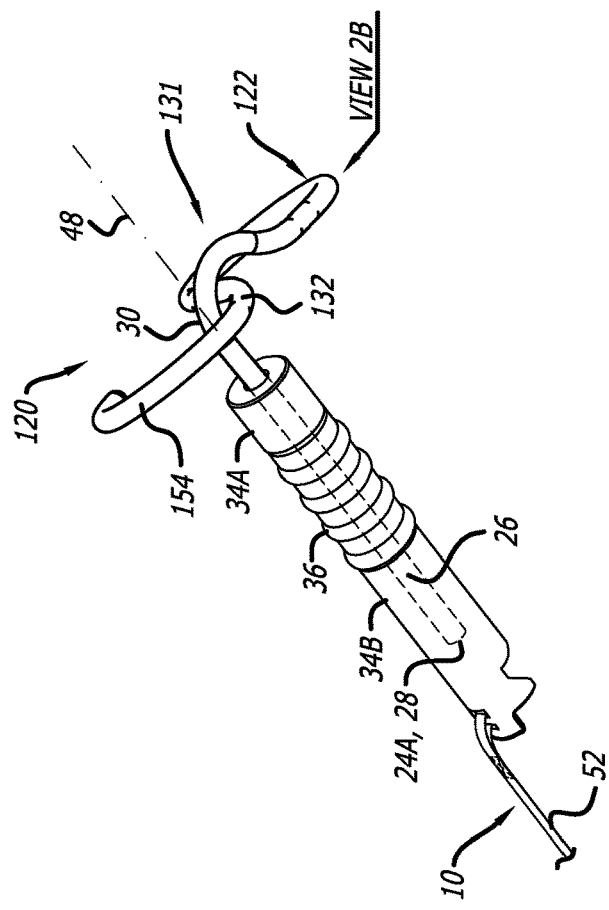
FIG. 2B
FIG. 2A

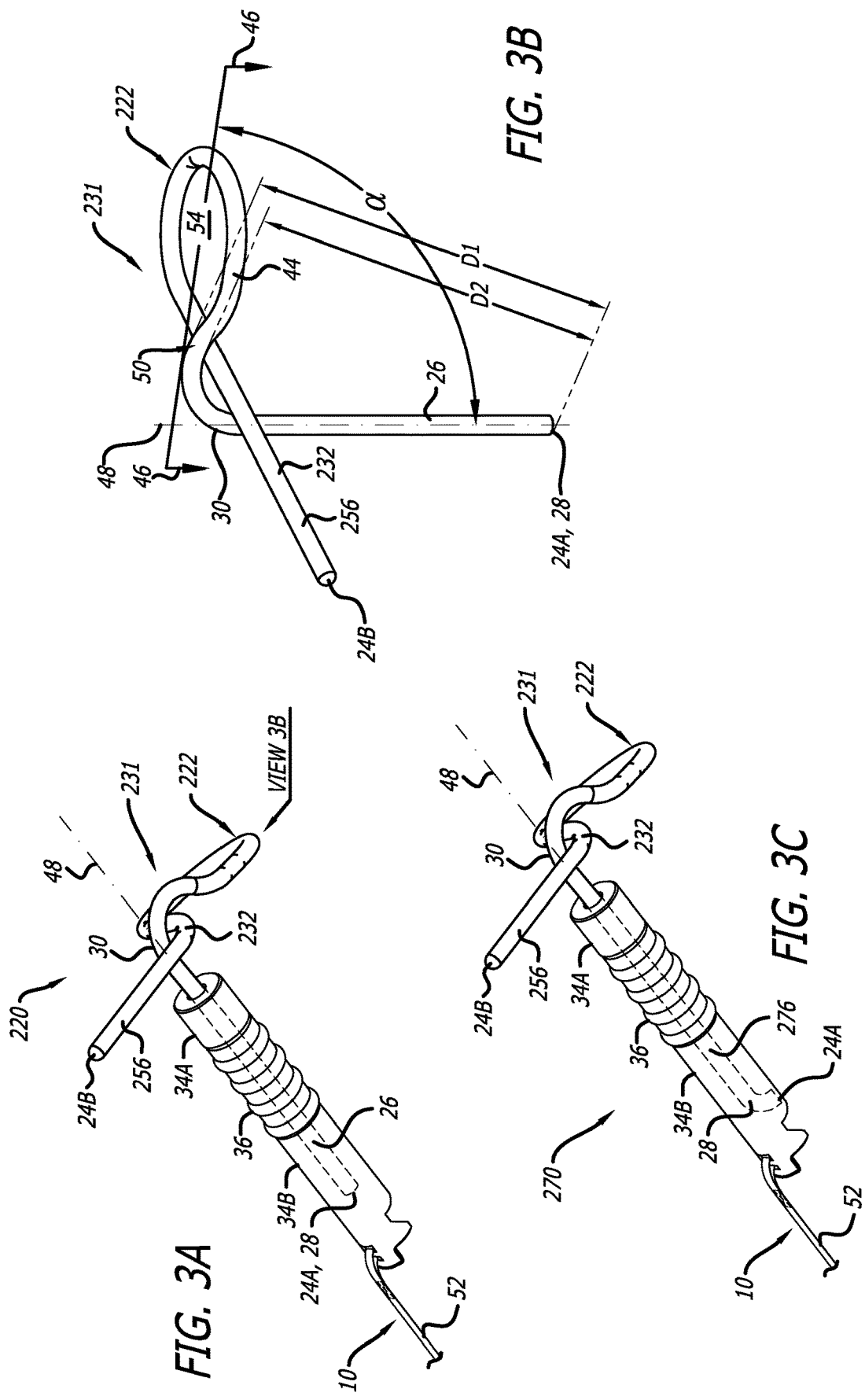

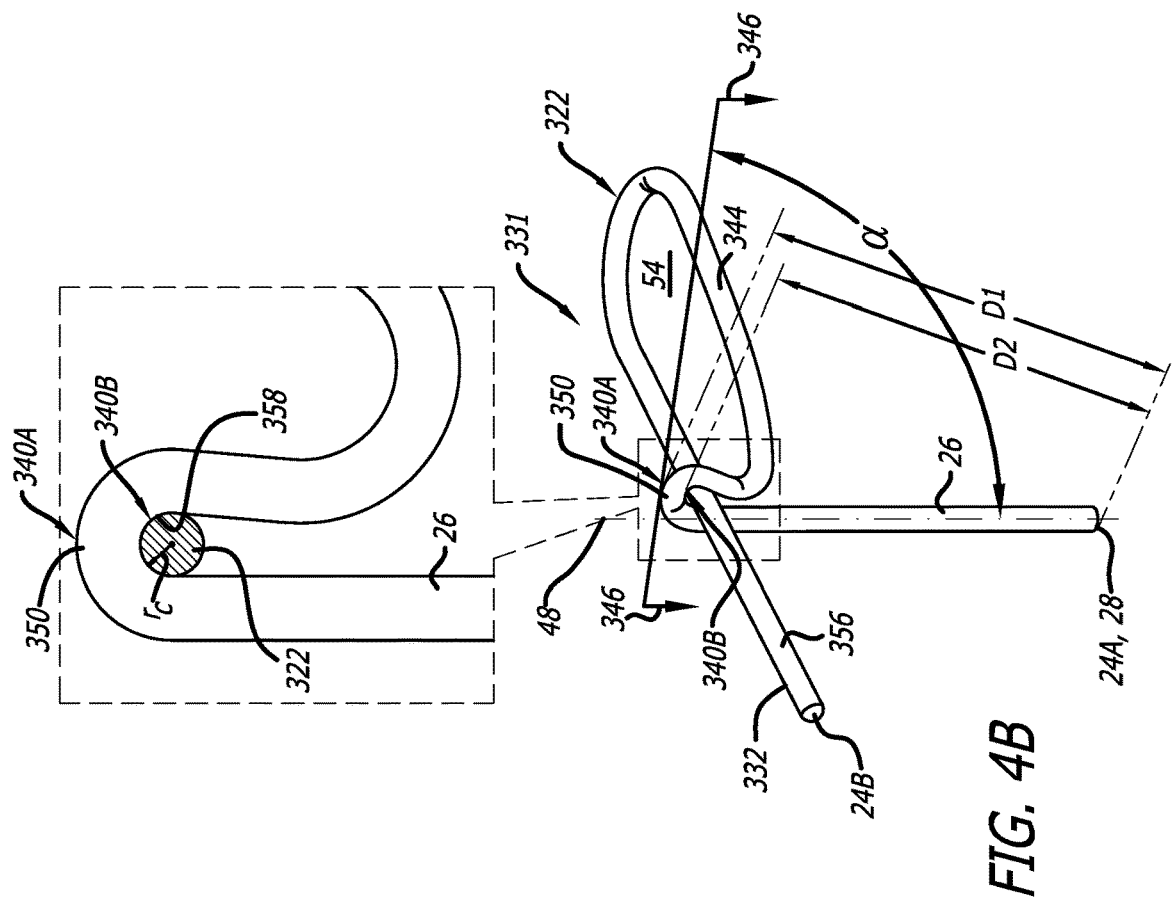
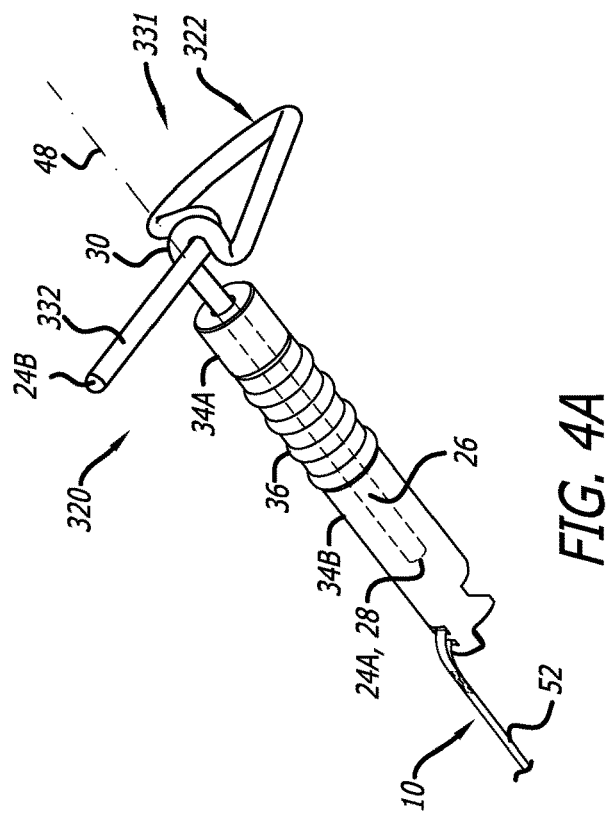
FIG. 4B
FIG. 4A

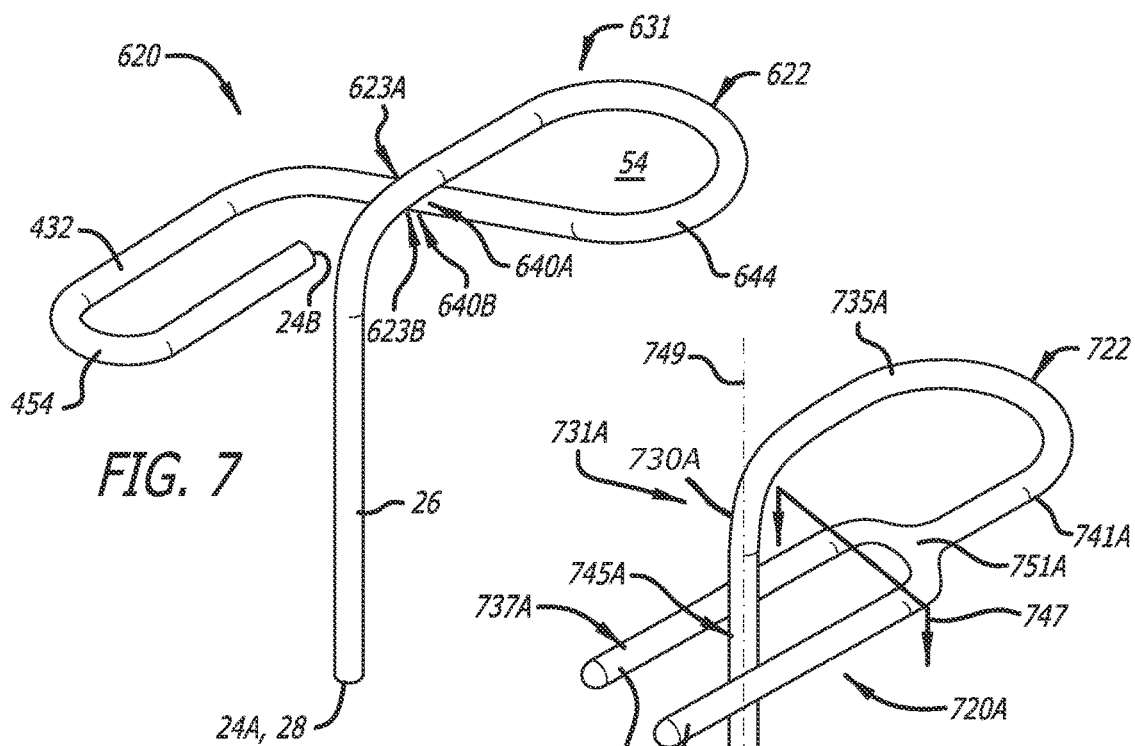

SELF-LOCKING TISSUE ANCHORS

CROSS-REFERENCE TO RELATED APPLICATIONS

The present application is the US National Stage of International Application PCT/US2019/068009, filed Dec. 20, 2019, which claims priority from U.S. Provisional Application 62/784,670, filed Dec. 24, 2018, which is assigned to the assignee of the present application and incorporated herein by reference.

FIELD OF THE APPLICATION

The present invention relates generally to tissue anchors, and specifically to tissue anchors for implantation at cardiac sites.

BACKGROUND OF THE APPLICATION

Tissue anchors are used for anchoring elements, such as pacemaker electrode leads or sutures, to tissue, such as bone or soft tissue. PCT Publication WO 2016/087934 to Gilmore et al., which is incorporated in its entirety herein by reference, describes a tissue anchor that includes a shaft, a tissue-coupling element, and a flexible elongate tension member. The tissue-coupling element includes a wire, which is shaped as an open loop coil having, in some applications, more than one coil revolution when the tissue anchor is unconstrained, i.e., expanded from a linear state to a coiled state. The tension member includes a distal portion, that is fixed to a site on the open loop coil, a proximal portion, which has a longitudinal segment that runs alongside at least a portion of the shaft, and a crossing portion, which (i) is disposed between the distal and the proximal portions along the tension member, and (ii) crosses at least a portion of the open loop when the tissue anchor is expanded. The tissue anchor is configured to allow relative axial motion between the at least a portion of the shaft and the longitudinal segment of the proximal portion of the tension member when the tissue anchor is expanded. For some applications, a head of the tissue anchor is shaped so as to define a passage in which the proximal portion of the flexible elongate tension member is slidably disposed. The flexible elongate tension member comprises a locking stopper, which is axially fixed to the proximal or the crossing portion of the flexible elongate tension member. The locking stopper and the passage are sized and shaped such that the size and shape of the passage prevent proximal movement of the locking stopper past the passage. The locking stopper limits the total load that can be applied to the open loop by the flexible elongate tension member, thereby reducing excessive, unnecessary strain on the open loop. Additional load (tension) that is applied by the flexible elongate tension member pulls on the entire anchor, and does not further increase the load applied across the open loop.

US Patent Application Publication 2003/0093096 to McGuckin, Jr. et al. describes a clip apparatus for closing a vessel aperture resulting from insertion of a surgical implement comprising an elongated strand comprising a central portion and extremity portions extending from the central portion. The tips of the extremity portions remote from the central portion are shaped to retain tissue encountered thereby. The extremity portions have memory characteristics seeking to cause the extremity portions to curl with respect to the central portions to retain tissue engaged thereby when the strand is in an unconstrained disposition.

U.S. Pat. No. 8,398,672 to Kleshinski et al. describes techniques for anchoring a medical implant device within a blood vessel or other body passageway. An anchor delivery system houses one or more expandable anchors connected to the medical implant device. The anchors remain housed in a non-expanded configuration until the medical implant device has been placed in a desired position within the body, and then the anchors are propelled through a body wall where each anchor expands outwardly from an anchor shaft. In one configuration, each anchor is formed as a compressible closed loop which extends outwardly from an anchor shaft and loops back to cross over and extend beyond the anchor shaft. To propel the anchors, a drive shaft is connected to a triggering unit which, when activated, causes the drive shaft to drive the anchor shafts in a direction such that the anchors are propelled through the body wall.

US Patent Application Publication 2002/0013571 to Goldfarb et al. describes techniques for grasping, and optional repositioning and fixation of the valve leaflets to treat cardiac valve regurgitation, particularly mitral valve regurgitation. Such grasping will typically be atraumatic providing a number of benefits. For example, atraumatic grasping may allow repositioning of the devices relative to the leaflets and repositioning of the leaflets themselves without damage to the leaflets. However, in some cases it may be necessary or desired to include grasping which pierces or otherwise permanently affects the leaflets. In some of these cases, the grasping step includes fixation. In one embodiment, described with reference to FIGS. 24 and 25, the anchor is comprised of a wire curved into a ring shape. The wire may be stainless steel, nitinol or other shape memory wire, polymer or similar material. A suture is attached to the center of the ring by a bonding material. The wire has a first end and a second end, wherein the first end is disposed on top of the ring and the second end is disposed underneath the ring. This configuration provides support for the ring when the anchor is pulled snuggly against a valve leaflet surface by the suture. The anchor may be used for fixation of valve leaflets. When the anchor wire is comprised of flexible materials, the anchor is collapsible for loading within a needle.

US Patent Application Publication 2014/0275756 to Bender et al. describes techniques for compressing, cutting, incising, reconfiguring, remodeling, attaching, repositioning, supporting, dislocating or altering the composition of tissues or anatomical structures to alter their positional or force relationship to other tissues or anatomical structures. In one embodiment, described with reference to FIGS. 9C and 9C', an anchor is provided that does not have a preformed coil at its distal tip, but instead a distal coil is custom-formed by the features at the end of a delivery member. FIG. 9C' depicts the anchor in place in tissue, and including a proximal tail that is also formed by the delivery member.

US Patent Application Publication 2009/0112052 to Lund et al. describes an implant for placement in the retropubic space of a patient. FIG. 8 is a perspective view of an implant that is anchored to the endopelvic fascia with an anchor, and FIG. 9 is a perspective view of one embodiment of a deployable member or anchor.

SUMMARY OF THE APPLICATION

Embodiments of the present invention provide tissue anchors that are deliverable to a cardiac chamber in an unexpanded generally elongate configuration within a deployment tool. The tissue anchors are configured to be anchored to a cardiac tissue wall at a target site such that a tensile force can be applied to the tissue anchors and thus to the cardiac tissue wall, once the tissue anchors are deployed, so as to move the cardiac tissue wall at the target site relative to adjacent cardiac tissue. For some applications, such motion alters the geometry of a cardiac valve, such as the tricuspid valve or the mitral valve.

In some embodiment of the present invention, a tissue anchor is provided that comprises a metal wire that has first and second wire ends and is shaped so as to define a straight anchor-shaft portion and a tissue-coupling portion, which extends from a distal end of the straight anchor-shaft portion, such that the straight anchor-shaft portion is disposed along the wire between the tissue-coupling portion and the first wire end. The tissue anchor is configured such that when the tissue-coupling portion is in an unconstrained state:

- the tissue-coupling portion is shaped so as to define a tail end portion that includes the second end of the wire,
- the tissue-coupling portion of the wire crosses itself at first and second loop-end longitudinal portions along the wire, so as to define a looped portion, which generally defines a looped-portion plane that forms an angle of between 75 and 90 degrees with an anchor-shaft axis of the straight anchor-shaft portion,
- the first loop-end longitudinal portion is closer to the first wire end along the wire than the second loop-end longitudinal portion is to the first wire end along the wire, and
- a greatest absolute distance between the first loop-end longitudinal portion and the first wire end is greater than a greatest absolute distance between the second loop-end longitudinal portion and the first wire end.

For some applications, the tissue anchor is configured such that when a proximal end of the straight anchor-shaft portion is pulled along the anchor-shaft axis away from the looped-portion plane, mechanical contact between the first and the second loop-end longitudinal portions locks the looped portion and prevents the looped portion from straightening as a result of the applied tension. Typically, the above-mentioned pulling is performed using a tether coupled to the tissue anchor.

In other embodiments of the present invention, a tissue anchor is provided that comprises a straight anchor-shaft portion and a tissue-coupling portion. The tissue anchor is configured such that when the tissue-coupling portion is in an unconstrained state in which the tissue-coupling portion is not constrained by any external forces:

- the tissue-coupling portion is shaped so as to define an elongate intermediate portion that extends from a distal end of the straight anchor-shaft portion, and a forked distal portion that extends from a distal end of the intermediate portion and defines two tines, and
- a tine-passing portion of the tissue anchor passes between the two tines, the tine-passing portion defined by the straight anchor-shaft portion and/or the intermediate portion.

For some applications, the tissue anchor is configured such that when the tissue-coupling portion is in the unconstrained state, the intermediate portion is not in mechanical contact with itself or with either of the two tines. When a proximal end of the straight anchor-shaft portion is pulled, along an anchor-shaft axis of the straight anchor-shaft portion, away from a tine plane generally defined by the two tines, the intermediate portion comes in mechanical contact with the intermediate portion and/or at least one of the two tines.

There is therefore provided, in accordance with an Inventive Concept 1 of the present invention, a tissue anchor including a metal wire that has exactly two wire ends,
wherein the wire is shaped so as to define:
- a straight anchor-shaft portion, and
- a tissue-coupling portion, which extends from a distal end of the straight anchor-shaft portion, such that the straight anchor-shaft portion is disposed along the wire between the tissue-coupling portion and a first of the exactly two wire ends, wherein the tissue anchor is configured such that when the tissue-coupling portion of the wire is in an unconstrained state in which the tissue-coupling portion is not constrained by any external forces:
- (a) the tissue-coupling portion of the wire is shaped so as to define a tail end portion that includes a second of the exactly two wire ends,
- (b) the tissue-coupling portion of the wire crosses itself at first and second loop-end longitudinal portions along the wire, so as to define a looped portion, which generally defines a looped-portion plane that forms an angle of between 75 and 90 degrees with an anchor-shaft axis of the straight anchor-shaft portion,
- (c) the first loop-end longitudinal portion is closer to the first wire end along the wire than the second loop-end longitudinal portion is to the first wire end along the wire, and
- (d) a greatest absolute distance between the first loop-end longitudinal portion and the first wire end is greater than a greatest absolute distance between the second loop-end longitudinal portion and the first wire end.

Inventive Concept 2. The tissue anchor according to Inventive Concept 1, wherein the tissue anchor is configured such that when the tissue-coupling portion of the wire is in the unconstrained state, the anchor-shaft axis does not pass through a space surrounded by and defined by the looped portion.

Inventive Concept 3. The tissue anchor according to Inventive Concept 1, wherein the tissue anchor is configured such that when the tissue-coupling portion of the wire is in the unconstrained state, the wire crosses itself exactly once, at the first and the second loop-end longitudinal portions along the wire.

Inventive Concept 4. The tissue anchor according to Inventive Concept 1, wherein the tissue anchor is configured such that when the tissue-coupling portion of the wire is in the unconstrained state, the wire defines only a single looped portion.

Inventive Concept 5. The tissue anchor according to Inventive Concept 1, wherein the wire is not shaped so as to define any looped portions proximal to a proximal end of the straight anchor-shaft portion.

Inventive Concept 6. The tissue anchor according to Inventive Concept 1, wherein the tissue anchor is configured such that:
- when the tissue-coupling portion of the wire is in the unconstrained state, the looped portion is shaped as an open looped portion in which the first and the second loop-end longitudinal portions are not in mechanical contact with each other, and
- when a proximal end of the straight anchor-shaft portion is pulled along the anchor-shaft axis away from the looped-portion plane, the first and the second loop-end longitudinal portions come in mechanical contact with each other.

Inventive Concept 7. The tissue anchor according to Inventive Concept 1, wherein when the tissue-coupling portion of the wire is in the unconstrained state, the tail end portion generally falls in the looped-portion plane.

Inventive Concept 8. The tissue anchor according to Inventive Concept 1, wherein when the tissue-coupling portion of the wire is in the unconstrained state, no portion of the tail end portion is parallel to the straight anchor-shaft portion.

Inventive Concept 9. The tissue anchor according to Inventive Concept 1, wherein the tissue anchor is configured such that when the tissue-coupling portion of the wire is in the unconstrained state, the tail end portion is shaped so as to define at least one straight portion.

Inventive Concept 10. The tissue anchor according to Inventive Concept 1, further including a fabric that covers a portion of the wire including the first loop-end longitudinal portion or the second loop-end longitudinal portion.

Inventive Concept 11. The tissue anchor according to Inventive Concept 1, wherein the tissue anchor is configured such that when the tissue-coupling portion of the wire is in the unconstrained state, the tail end portion is shaped so as to define at least one tail-end-portion curved portion.

Inventive Concept 12. The tissue anchor according to Inventive Concept 1, wherein a proximal end of the straight anchor-shaft portion is at the first of the exactly two wire ends.

Inventive Concept 13. The tissue anchor according to any one of Inventive Concepts 1-11, wherein a proximal end of the straight anchor-shaft portion is at the first of the exactly two wire ends.

Inventive Concept 14. The tissue anchor according to any one of Inventive Concepts 1-12, wherein the tissue anchor is configured such that when the tissue-coupling portion of the wire is in the unconstrained state, the tissue-coupling portion of the wire is shaped so as to define a first-loop-end curved portion along which the first loop-end longitudinal portion is located.

Inventive Concept 15. The tissue anchor according to Inventive Concept 14, wherein the tissue anchor is configured such that when a proximal end of the straight anchor-shaft portion is pulled along the anchor-shaft axis away from the looped-portion plane, the wire, at the second loop-end longitudinal portion, snaps into the first loop-end longitudinal portion at the first-loop-end curved portion of the wire.

Inventive Concept 16. The tissue anchor according to Inventive Concept 14, wherein the tissue anchor is configured such that when the tissue-coupling portion of the wire is in the unconstrained state, an inner curved surface of the first-loop-end curved portion has a radius of curvature equal to between 80% and 120% of a radius of the wire along the second loop-end longitudinal portion.

Inventive Concept 17. The tissue anchor according to Inventive Concept 14, wherein the first-loop-end curved portion extends directly from the distal end of the straight anchor-shaft portion.

Inventive Concept 18. The tissue anchor according to any one of Inventive Concepts 1-12, wherein the tissue anchor is configured such that when the tissue-coupling portion of the wire is in the unconstrained state, the tissue-coupling portion of the wire is shaped so as to define a first-loop-end straight portion along which the first loop-end longitudinal portion is located.

Inventive Concept 19. The tissue anchor according to Inventive Concept 18, wherein the tissue anchor is configured such that when the tissue-coupling portion of the wire is in the unconstrained state, the tissue-coupling portion of the wire is shaped so as to define a second-loop-end straight portion along which the second loop-end longitudinal portion is located.

Inventive Concept 20. The tissue anchor according to any one of Inventive Concepts 1-12, wherein the tissue anchor is configured such that when the tissue-coupling portion of the wire is in the unconstrained state, the looped portion includes exactly one turn.

Inventive Concept 21. The tissue anchor according to any one of Inventive Concepts 1-12, further including an anchor head that is coupled to and supports the straight anchor-shaft portion of the wire.

Inventive Concept 22. A system including the tissue anchor according to any one of Inventive Concept 1-12, wherein the system further includes a tether affixed to the tissue anchor.

Inventive Concept 23. The system according to Inventive Concept 22, wherein the tissue anchor is a first tissue anchor, and wherein the system further includes a second tissue anchor, which is separate and distinct from the first tissue anchor, and which is coupled to the first tissue anchor by the tether.

There is further provided, in accordance with an Inventive Concept 24 of the present invention, a method including:
  delivering, to a cardiac chamber, within a deployment tool, a tissue anchor including a metal wire that has exactly two wire ends, the wire shaped so as to define a straight anchor-shaft portion and a tissue-coupling portion that is in an unexpanded generally elongate configuration within the deployment tool, the tissue-coupling portion extending from a distal end of the straight anchor-shaft portion, such that the straight anchor-shaft portion is disposed along the wire between the tissue-coupling portion and a first of the exactly two wire ends;
  delivering the tissue-coupling portion of the wire in the unexpanded generally elongate configuration through a cardiac tissue wall from a first side of the cardiac tissue wall to a second farther side of the cardiac tissue wall; and
  releasing the tissue anchor from the deployment tool such that:
    (a) the straight anchor-shaft portion of the wire is disposed at least partially within the cardiac tissue wall,
    (b) the tissue-coupling portion of the wire is disposed outside the second farther side of the cardiac tissue wall, the tissue-coupling portion shaped to as to define a tail end portion that includes a second of the exactly two wire ends,
    (c) the tissue-coupling portion the wire crosses itself at first and second loop-end longitudinal portions along the wire, so as to define a looped portion that anchors the tissue anchor to the cardiac tissue wall, the looped portion generally defining a looped-portion plane that forms an angle of between 75 and 90 degrees with an anchor-shaft axis of the straight anchor-shaft portion,
    (d) the first loop-end longitudinal portion is closer to the first wire end along the wire than the second loop-end longitudinal portion is to the first wire end along the wire, and
    (e) a greatest absolute distance between the first loop-end longitudinal portion and the first wire end is greater than a greatest absolute distance between the second loop-end longitudinal portion and the first wire end.

Inventive Concept 25. The method according to Inventive Concept 24, wherein a proximal end of the straight anchor-shaft portion is at the first of the exactly two wire ends.

Inventive Concept 26. The method according to Inventive Concept 24, further including, after releasing the tissue anchor from the deployment tool, applying tension to the tissue anchor by pulling a proximal end of the straight anchor-shaft portion along the anchor-shaft axis away from the looped-portion plane.

Inventive Concept 27. The method according to Inventive Concept 26,
wherein releasing the tissue anchor from the deployment tool includes releasing the tissue anchor from the deployment tool such that the looped portion is shaped as an open looped portion in which the first and the second loop-end longitudinal portions are not in mechanical contact with each other, and
wherein pulling the proximal end of the straight anchor-shaft portion along the anchor-shaft axis away from the looped-portion plane brings the first and the second loop-end longitudinal portions in mechanical contact with each other.

Inventive Concept 28. The method according to Inventive Concept 26,
wherein releasing the tissue anchor from the deployment tool includes releasing the tissue anchor from the deployment tool such that the tissue-coupling portion of the wire is shaped so as to define a first-loop-end curved portion along which the first loop-end longitudinal portion is located, and
wherein pulling the proximal end of the straight anchor-shaft portion along the anchor-shaft axis away from the looped-portion plane snaps the wire, at the second loop-end longitudinal portion, into the first loop-end longitudinal portion at the first-loop-end curved portion of the wire.

Inventive Concept 29. The method according to Inventive Concept 28, wherein releasing the tissue anchor from the deployment tool includes releasing the tissue anchor from the deployment tool such that an inner curved surface of the first-loop-end curved portion has a radius of curvature equal to between 80% and 120% of a radius of the wire along the second loop-end longitudinal portion.

Inventive Concept 30. The method according to Inventive Concept 28, wherein the first-loop-end curved portion extends directly from the distal end of the straight anchor-shaft portion.

Inventive Concept 31. The method according to Inventive Concept 26, wherein pulling the proximal end of the straight anchor-shaft portion along the anchor-shaft axis away from the looped-portion plane tightly draws the looped portion against the second far side of the cardiac tissue wall.

Inventive Concept 32. The method according to Inventive Concept 26, wherein pulling the proximal end of the straight anchor-shaft portion along the anchor-shaft axis away from the looped-portion plane includes pulling a tether affixed to the tissue anchor.

Inventive Concept 33. The method according to Inventive Concept 32, wherein the tissue anchor is a first tissue anchor, and wherein the method further includes implanting a second tissue anchor, which is separate and distinct from the first tissue anchor, and which is coupled to the first tissue anchor by the tether.

Inventive Concept 34. The method according to Inventive Concept 24, wherein the cardiac tissue wall is a myocardial tissue wall, and wherein delivering the tissue-coupling portion of the wire in the unexpanded generally elongate configuration through the cardiac tissue wall includes delivering the tissue-coupling portion of the wire through the myocardial tissue wall into the pericardial cavity between visceral pericardium and parietal pericardium, generally alongside and against the parietal pericardium, without penetrating the parietal pericardium.

Inventive Concept 35. The method according to Inventive Concept 24, wherein releasing the tissue anchor from the deployment tool includes releasing the tissue anchor from the deployment tool such that the anchor-shaft axis does not pass through a space surrounded by and defined by the looped portion.

Inventive Concept 36. The method according to Inventive Concept 24, wherein releasing the tissue anchor from the deployment tool includes releasing the tissue anchor from the deployment tool such that the wire crosses itself exactly once, at the first and the second loop-end longitudinal portions along the wire.

Inventive Concept 37. The method according to Inventive Concept 24, wherein releasing the tissue anchor from the deployment tool includes releasing the tissue anchor from the deployment tool such that the wire defines only a single looped portion.

Inventive Concept 38. The method according to Inventive Concept 24, wherein the wire is not shaped so as to define any looped portions proximal to a proximal end of the straight anchor-shaft portion.

Inventive Concept 39. The method according to Inventive Concept 24, wherein releasing the tissue anchor from the deployment tool includes releasing the tissue anchor from the deployment tool such that the tissue-coupling portion of the wire is shaped so as to define a first-loop-end straight portion along which the first loop-end longitudinal portion is located.

Inventive Concept 40. The method according to Inventive Concept 39, wherein releasing the tissue anchor from the deployment tool includes releasing the tissue anchor from the deployment tool such that the tissue-coupling portion of the wire is shaped so as to define a second-loop-end straight portion along which the second loop-end longitudinal portion is located.

Inventive Concept 41. The method according to Inventive Concept 24, wherein releasing the tissue anchor from the deployment tool includes releasing the tissue anchor from the deployment tool such that the tail end portion generally falls in the looped-portion plane.

Inventive Concept 42. The method according to Inventive Concept 24, wherein releasing the tissue anchor from the deployment tool includes releasing the tissue anchor from the deployment tool such no portion of the tail end portion is parallel to the straight anchor-shaft portion.

Inventive Concept 43. The method according to Inventive Concept 24, wherein releasing the tissue anchor from the deployment tool includes releasing the tissue anchor from the deployment tool such that the tail end portion is shaped so as to define at least one straight portion.

Inventive Concept 44. The method according to Inventive Concept 24, wherein releasing the tissue anchor from the deployment tool includes releasing the tissue anchor from the deployment tool such that the tail end portion is shaped so as to define at least one tail-end-portion curved portion.

Inventive Concept 45. The method according to Inventive Concept 24, wherein the tissue anchor further includes a fabric that covers a portion of the wire including the first loop-end longitudinal portion or the second loop-end longitudinal portion.

Inventive Concept 46. The method according to Inventive Concept 24, wherein releasing the tissue anchor from the deployment tool includes releasing the tissue anchor from the deployment tool such that the looped portion includes exactly one turn.

Inventive Concept 47. The method according to Inventive Concept 24, wherein the tissue anchor further includes an anchor head that is coupled to and supports the straight anchor-shaft portion of the wire.

There is still further provided, in accordance with an Inventive Concept 48 of the present invention, a tissue anchor including a metal wire that has exactly two wire ends, wherein the wire is shaped so as to define:
  a straight anchor-shaft portion, and
  a tissue-coupling portion, which extends from a distal end of the straight anchor-shaft portion, such that the straight anchor-shaft portion is disposed along the wire between the tissue-coupling portion and a first of the exactly two wire ends,
wherein the tissue anchor is configured such that when the tissue-coupling portion of the wire is in an unconstrained state in which the tissue-coupling portion is not constrained by any external forces:
  (a) the tissue-coupling portion of the wire is shaped so as to define a tail end portion that includes a second of the exactly two wire ends, and
  (b) the tissue-coupling portion of the wire crosses itself at first and second loop-end longitudinal portions along the wire, so as to define a looped portion, which generally defines a looped-portion plane that forms an angle of between 75 and 90 degrees with an anchor-shaft axis of the straight anchor-shaft portion, and
wherein the tissue anchor is configured such that when a proximal end of the straight anchor-shaft portion is pulled along the anchor-shaft axis away from the looped-portion plane, mechanical contact between the first and the second loop-end longitudinal portions locks the looped portion and prevents the looped portion from straightening as a result of tension applied to the straight anchor-shaft portion.

Inventive Concept 49. The tissue anchor according to Inventive Concept 48, wherein the proximal end of the straight anchor-shaft portion is at the first of the exactly two wire ends.

Inventive Concept 50. The tissue anchor according to Inventive Concept 48, wherein the tissue anchor is configured such that when the tissue-coupling portion of the wire is in the unconstrained state, the anchor-shaft axis does not pass through a space surrounded by and defined by the looped portion.

Inventive Concept 51. The tissue anchor according to Inventive Concept 48, wherein the tissue anchor is configured such that:
  when the tissue-coupling portion of the wire is in the unconstrained state, the looped portion is shaped as an open looped portion in which the first and the second loop-end longitudinal portions are not in the mechanical contact with each other, and
  when a proximal end of the straight anchor-shaft portion is pulled along the anchor-shaft axis away from the looped-portion plane, the first and the second loop-end longitudinal portions come in the mechanical contact with each other.

Inventive Concept 52. The tissue anchor according to Inventive Concept 48, wherein the tissue anchor is configured such that when the tissue-coupling portion of the wire is in the unconstrained state, the wire crosses itself exactly once, at the first and the second loop-end longitudinal portions along the wire.

Inventive Concept 53. The tissue anchor according to Inventive Concept 48, wherein the tissue anchor is configured such that when the tissue-coupling portion of the wire is in the unconstrained state, the wire defines only a single looped portion.

Inventive Concept 54. The tissue anchor according to Inventive Concept 48, wherein the wire is not shaped so as to define any looped portions proximal to the proximal end of the straight anchor-shaft portion.

Inventive Concept 55. The tissue anchor according to Inventive Concept 48, wherein when the tissue-coupling portion of the wire is in the unconstrained state, the tail end portion generally falls in the looped-portion plane.

Inventive Concept 56. The tissue anchor according to Inventive Concept 48, wherein when the tissue-coupling portion of the wire is in the unconstrained state, no portion of the tail end portion is parallel to the straight anchor-shaft portion.

Inventive Concept 57. The tissue anchor according to Inventive Concept 48, wherein the tissue anchor is configured such that when the tissue-coupling portion of the wire is in the unconstrained state, the tail end portion is shaped so as to define at least one straight portion.

Inventive Concept 58. The tissue anchor according to Inventive Concept 48, wherein the tissue anchor is configured such that when the tissue-coupling portion of the wire is in the unconstrained state, the tail end portion is shaped so as to define at least one tail-end-portion curved portion.

Inventive Concept 59. The tissue anchor according to any one of Inventive Concepts 48-58, wherein the tissue anchor is configured such that when the tissue-coupling portion of the wire is in the unconstrained state, the tissue-coupling portion of the wire is shaped so as to define a first-loop-end curved portion along which the first loop-end longitudinal portion is located.

Inventive Concept 60. The tissue anchor according to Inventive Concept 59, wherein the tissue anchor is configured such that when the proximal end of the straight anchor-shaft portion is pulled along the anchor-shaft axis away from the looped-portion plane, the wire, at the second loop-end longitudinal portion, snaps into the first loop-end longitudinal portion at the first-loop-end curved portion of the wire, thereby locking the looped portion.

Inventive Concept 61. The tissue anchor according to Inventive Concept 59, wherein the tissue anchor is configured such that when the tissue-coupling portion of the wire is in the unconstrained state, an inner curved surface of the first-loop-end curved portion has a radius of curvature equal to between 80% and 120% of a radius of the wire along the second loop-end longitudinal portion.

Inventive Concept 62. The tissue anchor according to Inventive Concept 59, wherein the first-loop-end curved portion extends directly from the distal end of the straight anchor-shaft portion.

Inventive Concept 63. The tissue anchor according to any one of Inventive Concepts 48-58, wherein the tissue anchor is configured such that when the tissue-coupling portion of the wire is in the unconstrained state, the tissue-coupling portion of the wire is shaped so as to define a first-loop-end straight portion along which the first loop-end longitudinal portion is located.

Inventive Concept 64. The tissue anchor according to Inventive Concept 63, wherein the tissue anchor is configured such that when the tissue-coupling portion of the wire is in the unconstrained state, the tissue-coupling portion of the wire is shaped so as to define a second-loop-end straight portion along which the second loop-end longitudinal portion is located.

Inventive Concept 65. The tissue anchor according to any one of Inventive Concepts 48-58, further including a fabric that covers a portion of the wire including the first loop-end longitudinal portion or the second loop-end longitudinal portion.

Inventive Concept 66. The tissue anchor according to any one of Inventive Concepts 48-58, wherein the tissue anchor is configured such that when the tissue-coupling portion of the wire is in the unconstrained state, the looped portion includes exactly one turn.

Inventive Concept 67. The tissue anchor according to any one of Inventive Concepts 48-58, further including an anchor head that is coupled to and supports the straight anchor-shaft portion of the wire.

Inventive Concept 68. A system including the tissue anchor according to any one of Inventive Concepts 48-58, wherein the system further includes a tether affixed to the tissue anchor.

Inventive Concept 69. The system according to Inventive Concept 68, wherein the tissue anchor is a first tissue anchor, and wherein the system further includes a second tissue anchor, which is separate and distinct from the first tissue anchor, and which is coupled to the first tissue anchor by the tether.

There is additionally provided, in accordance with an Inventive Concept 70 of the present invention, a method including:
delivering, to a cardiac chamber, within a deployment tool, a tissue anchor including a metal wire that has exactly two wire ends, the wire shaped so as to define a straight anchor-shaft portion and a tissue-coupling portion that is in an unexpanded generally elongate configuration within the deployment tool, the tissue-coupling portion extending from a distal end of the straight anchor-shaft portion, such that the straight anchor-shaft portion is disposed along the wire between the tissue-coupling portion and a first of the exactly two wire ends;
delivering the tissue-coupling portion of the wire in the unexpanded generally elongate configuration through a cardiac tissue wall from a first side of the cardiac tissue wall to a second farther side of the cardiac tissue wall;
releasing the tissue anchor from the deployment tool such that:
(a) the straight anchor-shaft portion of the wire is disposed at least partially within the cardiac tissue wall,
(b) the tissue-coupling portion of the wire is disposed outside the second farther side of the cardiac tissue wall, the tissue-coupling portion shaped to as to define a tail end portion that includes a second of the exactly two wire ends,
(c) the tissue-coupling portion the wire crosses itself at first and second loop-end longitudinal portions along the wire, so as to define a looped portion, such that the looped portion anchors the tissue anchor to the cardiac tissue wall, and the looped portion generally defines a looped-portion plane that forms an angle of between 75 and 90 degrees with an anchor-shaft axis of the straight anchor-shaft portion; and
after releasing the tissue anchor from the deployment tool, applying tension to the tissue anchor by pulling a proximal end of the straight anchor-shaft portion along the anchor-shaft axis away from the looped-portion plane, such that mechanical contact between the first and the second loop-end longitudinal portions locks the looped portion and prevents the looped portion from straightening as a result of tension applied to the straight anchor-shaft portion.

Inventive Concept 71. The method according to Inventive Concept 70, wherein a proximal end of the straight anchor-shaft portion is at the first of the exactly two wire ends.

Inventive Concept 72. The method according to Inventive Concept 70,
wherein releasing the tissue anchor from the deployment tool includes releasing the tissue anchor from the deployment tool such that the looped portion is shaped as an open looped portion in which the first and the second loop-end longitudinal portions are not in mechanical contact with each other, and
wherein pulling the proximal end of the straight anchor-shaft portion along the anchor-shaft axis away from the looped-portion plane brings the first and the second loop-end longitudinal portions in mechanical contact with each other.

Inventive Concept 73. The method according to Inventive Concept 70,
wherein releasing the tissue anchor from the deployment tool includes releasing the tissue anchor from the deployment tool such that the tissue-coupling portion of the wire is shaped so as to define a first-loop-end curved portion along which the first loop-end longitudinal portion is located, and
wherein pulling the proximal end of the straight anchor-shaft portion along the anchor-shaft axis away from the looped-portion plane snaps the wire, at the second loop-end longitudinal portion, into the first loop-end longitudinal portion at the first-loop-end curved portion of the wire, thereby locking the looped portion.

Inventive Concept 74. The method according to Inventive Concept 73, wherein releasing the tissue anchor from the deployment tool includes releasing the tissue anchor from the deployment tool such that an inner curved surface of the first-loop-end curved portion has a radius of curvature equal to between 80% and 120% of a radius of the wire along the second loop-end longitudinal portion.

Inventive Concept 75. The method according to Inventive Concept 73, wherein the first-loop-end curved portion extends directly from the distal end of the straight anchor-shaft portion.

Inventive Concept 76. The method according to Inventive Concept 70, wherein pulling the proximal end of the straight anchor-shaft portion along the anchor-shaft axis away from the looped-portion plane tightly draws the looped portion against the second far side of the cardiac tissue wall.

Inventive Concept 77. The method according to Inventive Concept 70, wherein pulling the proximal end of the straight anchor-shaft portion along the anchor-shaft axis away from the looped-portion plane includes pulling a tether affixed to the tissue anchor.

Inventive Concept 78. The method according to Inventive Concept 77, wherein the tissue anchor is a first tissue anchor, and wherein the method further includes implanting a second tissue anchor, which is separate and distinct from the first tissue anchor, and which is coupled to the first tissue anchor by the tether.

Inventive Concept 79. The method according to Inventive Concept 70, wherein the cardiac tissue wall is a myocardial tissue wall, and wherein delivering the tissue-coupling portion of the wire in the unexpanded generally elongate configuration through the cardiac tissue wall includes delivering the tissue-coupling portion of the wire through the myocardial tissue wall into the pericardial cavity between visceral pericardium and parietal pericardium, generally alongside and against the parietal pericardium, without penetrating the parietal pericardium.

Inventive Concept 80. The method according to Inventive Concept 70, wherein the tissue anchor further includes an anchor head that is coupled to and supports the straight anchor-shaft portion of the wire.

There is yet additionally provided, in accordance with an Inventive Concept 81 of the present invention, a tissue anchor including:

a straight anchor-shaft portion; and a tissue-coupling portion, wherein the tissue anchor is configured such that when the tissue-coupling portion is in an unconstrained state in which the tissue-coupling portion is not constrained by any external forces:

(a) the tissue-coupling portion is shaped so as to define (i) an elongate intermediate portion that extends from a distal end of the straight anchor-shaft portion, and (ii) a forked distal portion that extends from a distal end of the intermediate portion and defines two tines, and (b) a tine-passing portion of the tissue anchor passes between the two tines, the tine-passing portion defined by at least one of the group of portions consisting of: the straight anchor-shaft portion and the intermediate portion.

Inventive Concept 82. The tissue anchor according to Inventive Concept 81, wherein the tine-passing portion is defined by the straight anchor-shaft portion.

Inventive Concept 83. The tissue anchor according to Inventive Concept 81, wherein the tine-passing portion is defined by the intermediate portion.

Inventive Concept 84. The tissue anchor according to Inventive Concept 81, wherein the tissue anchor is configured such that when the tissue-coupling portion is in the unconstrained state, exactly one tine-passing portion of the tissue anchor passes between the two tines.

Inventive Concept 85. The tissue anchor according to Inventive Concept 81, wherein the tissue anchor is configured such that when the tissue-coupling portion is in the unconstrained state, the two tines generally define a tine plane that forms an angle of between 60 and 90 degrees with an anchor-shaft axis of the straight anchor-shaft portion.

Inventive Concept 86. The tissue anchor according to Inventive Concept 81, wherein the tissue anchor is configured such that when the tissue-coupling portion is in the unconstrained state, the intermediate portion is at least partially curved.

Inventive Concept 87. The tissue anchor according to Inventive Concept 81, further including a fabric that at least partially covers the tissue-coupling element.

Inventive Concept 88. The tissue anchor according to any one of Inventive Concepts 81-87, wherein the tissue anchor includes a single metal wire that is shaped so as to define the straight anchor-shaft portion and the tissue-coupling portion.

Inventive Concept 89. The tissue anchor according to Inventive Concept 88, wherein a proximal end of the straight anchor-shaft portion coincides with a proximal end of the wire.

Inventive Concept 90. The tissue anchor according to any one of Inventive Concepts 81-87, wherein the tissue anchor includes two metal wires that are shaped so as to together define the straight anchor-shaft portion and the tissue-coupling portion, and wherein the tissue anchor is configured such that when the tissue-coupling portion is in the unconstrained state, the two metal wires:

run alongside each other along at least a portion of the straight anchor-shaft portion and along at least a portion of the intermediate portion, and are separate from each other along the forked distal portion, such that the two wires respectively define the two tines.

Inventive Concept 91. The tissue anchor according to Inventive Concept 90, wherein the two metal wires are fixed to each other at least partially along the straight anchor-shaft portion and at least partially along the intermediate portion.

Inventive Concept 92. The tissue anchor according to Inventive Concept 90, wherein a proximal end of the straight anchor-shaft portion coincides with a proximal end of at least one of the two wires.

Inventive Concept 93. The tissue anchor according to any one of Inventive Concepts 81-87, wherein the tissue anchor is configured such that:

when the tissue-coupling portion is in the unconstrained state, the intermediate portion is not in mechanical contact with itself or with either of the two tines, and when a proximal end of the straight anchor-shaft portion is pulled, along an anchor-shaft axis of the straight anchor-shaft portion, away from a tine plane generally defined by the two tines, the intermediate portion comes in mechanical contact with at least one element selected from the group consisting of: the intermediate portion and at least one of the two tines.

Inventive Concept 94. The tissue anchor according to Inventive Concept 93, wherein the tissue anchor is configured such that when the proximal end of the straight anchor-shaft portion is pulled along the anchor-shaft axis away from the tine plane, the intermediate portion comes in mechanical contact with the tissue-coupling portion at a junction at which the tissue-coupling portion forks into the two tines.

Inventive Concept 95. The tissue anchor according to any one of Inventive Concepts 81-87, further including an anchor head that is coupled to and supports the straight anchor-shaft portion.

Inventive Concept 96. A system including the tissue anchor according to any one of Inventive Concepts 81-87, the system further including a tether affixed to the tissue anchor.

Inventive Concept 97. The system according to Inventive Concept 96, wherein the tissue anchor is a first tissue anchor, and wherein the system further includes a second tissue anchor, which is separate and distinct from the first tissue anchor, and which is coupled to the first tissue anchor by the tether.

There is also provided, in accordance with an Inventive Concept 98 of the present invention, a method including:

delivering, to a cardiac chamber, within a deployment tool, a tissue anchor including a straight anchor-shaft portion and a tissue-coupling portion that is in an unexpanded generally elongate configuration within the deployment tool;

delivering the tissue-coupling portion in the unexpanded generally elongate configuration through a cardiac tissue wall from a first side of the cardiac tissue wall to a second farther side of the cardiac tissue wall; and releasing the tissue anchor from the deployment tool such that:

(a) the straight anchor-shaft portion is disposed at least partially within the cardiac tissue wall, (b) the tissue-coupling portion is disposed outside the second farther side of the cardiac tissue wall, the tissue-coupling portion shaped (i) an elongate intermediate portion that extends from a distal end of the straight anchor-shaft portion, and (ii) a forked distal portion that extends from a distal end of the intermediate portion and defines two tines, and (c) a tine-passing portion of the tissue anchor passes between the two tines, the tine-passing portion defined by at least one of the group of portions consisting of: the straight anchor-shaft portion and the intermediate portion.

Inventive Concept 99. The method according to Inventive Concept 98, wherein releasing the tissue anchor from the deployment tool includes releasing the tissue anchor from the deployment tool such that the tine-passing portion is defined by the straight anchor-shaft portion.

Inventive Concept 100. The method according to Inventive Concept 98, wherein releasing the tissue anchor from the deployment tool includes releasing the tissue anchor from the deployment tool such that the tine-passing portion is defined by the intermediate portion.

Inventive Concept 101. The method according to Inventive Concept 98, wherein releasing the tissue anchor from the deployment tool includes releasing the tissue anchor from the deployment tool such that exactly one tine-passing portion of the tissue anchor passes between the two tines.

Inventive Concept 102. The method according to Inventive Concept 98, wherein the tissue anchor includes a single metal wire that is shaped so as to define the straight anchor-shaft portion and the tissue-coupling portion.

Inventive Concept 103. The method according to Inventive Concept 102, wherein a proximal end of the straight anchor-shaft portion coincides with a proximal end of the wire.

Inventive Concept 104. The method according to Inventive Concept 98,
wherein the tissue anchor includes two metal wires that are shaped so as to together define the straight anchor-shaft portion and the tissue-coupling portion, and
wherein releasing the tissue anchor from the deployment tool includes releasing the tissue anchor from the deployment tool such that the two metal wires:
run alongside each other along at least a portion of the straight anchor-shaft portion and along at least a portion of the intermediate portion, and
are separate from each other along the forked distal portion, such that the two wires respectively define the two tines.

Inventive Concept 105. The method according to Inventive Concept 104, wherein the two metal wires are fixed to each other at least partially along the straight anchor-shaft portion and at least partially along the intermediate portion.

Inventive Concept 106. The method according to Inventive Concept 104, wherein a proximal end of the straight anchor-shaft portion coincides with a proximal end of at least one of the two wires.

Inventive Concept 107. The method according to Inventive Concept 98, wherein releasing the tissue anchor from the deployment tool includes releasing the tissue anchor from the deployment tool such that the two tines generally define a tine plane that forms an angle of between 60 and 90 degrees with an anchor-shaft axis of the straight anchor-shaft portion.

Inventive Concept 108. The method according to Inventive Concept 98, wherein releasing the tissue anchor from the deployment tool includes releasing the tissue anchor from the deployment tool such that the intermediate portion is at least partially curved.

Inventive Concept 109. The method according to Inventive Concept 98, further including, after releasing the tissue anchor from the deployment tool, applying tension to the tissue anchor by pulling a proximal end of the straight anchor-shaft portion, along an anchor-shaft axis of the straight anchor-shaft portion, away from a tine plane generally defined by the two tines.

Inventive Concept 110. The method according to Inventive Concept 109,
wherein releasing the tissue anchor from the deployment tool includes releasing the tissue anchor from the deployment tool such that the intermediate portion is not in mechanical contact with itself or with either of the two tines, and
wherein pulling the proximal end of the straight anchor-shaft portion away from the tine plane brings the intermediate portion in mechanical contact with at least one element selected from the group consisting of: the intermediate portion and at least one of the two tines.

Inventive Concept 111. The method according to Inventive Concept 110, wherein pulling the proximal end of the straight anchor-shaft portion away from the tine plane brings the intermediate portion in mechanical contact with the tissue-coupling portion at a junction at which the tissue-coupling portion forks into the two tines.

Inventive Concept 112. The method according to Inventive Concept 109, wherein pulling the proximal end of the straight anchor-shaft portion along the anchor-shaft axis away from the tine plane tightly draws the tines against the second far side of the cardiac tissue wall.

Inventive Concept 113. The method according to Inventive Concept 109, wherein pulling the proximal end of the straight anchor-shaft portion along the anchor-shaft axis away from the tine plane includes pulling a tether affixed to the tissue anchor.

Inventive Concept 114. The method according to Inventive Concept 113, wherein the tissue anchor is a first tissue anchor, and wherein the method further includes implanting a second tissue anchor, which is separate and distinct from the first tissue anchor, and which is coupled to the first tissue anchor by the tether.

Inventive Concept 115. The method according to Inventive Concept 98, wherein the cardiac tissue wall is a myocardial tissue wall, and wherein delivering the tissue-coupling portion in the unexpanded generally elongate configuration through the cardiac tissue wall includes delivering the tissue-coupling portion through the myocardial tissue wall into the pericardial cavity between visceral pericardium and parietal pericardium, generally alongside and against the parietal pericardium, without penetrating the parietal pericardium.

Inventive Concept 116. The method according to Inventive Concept 98, wherein the tissue anchor further includes a fabric that at least partially covers the tissue-coupling element.

Inventive Concept 117. The method according to Inventive Concept 98, wherein the tissue anchor further includes an anchor head that is coupled to and supports the straight anchor-shaft portion.

There is further provided, in accordance with an Inventive Concept 118 of the present invention, a tissue anchor including a metal wire that has exactly two wire ends,
wherein the wire is shaped so as to define:

a straight anchor-shaft portion, which has (i) a proximal end at a first of the exactly two wire ends and (ii) a distal end, and a tissue-coupling portion, which extends from the distal end of the straight anchor-shaft portion, and wherein the tissue anchor is configured such that when the tissue-coupling portion of the wire is in an unconstrained state in which the tissue-coupling portion is not constrained by any external forces:

(a) the tissue-coupling portion of the wire is shaped so as to define a tail end portion that includes a second of the exactly two wire ends, (b) the tissue-coupling portion of the wire crosses itself at first and second loop-end longitudinal portions along the wire, so as to define a looped portion, which generally defines a looped-portion plane that forms an angle of between 75 and 90 degrees with an anchor-shaft axis of the straight anchor-shaft portion, (c) the first loop-end longitudinal portion is closer to the first wire end along the wire than the second loop-end longitudinal portion is to the first wire end along the wire, and (d) a greatest absolute distance between the first loop-end longitudinal portion and the first wire end is greater than a greatest absolute distance between the second loop-end longitudinal portion and the first wire end.

Inventive Concept 119. The tissue anchor according to Inventive Concept 118, wherein the tissue anchor is configured such that when the tissue-coupling portion of the wire is in the unconstrained state, the anchor-shaft axis does not pass through a space surrounded by and defined by the looped portion.

Inventive Concept 120. The tissue anchor according to Inventive Concept 118, wherein the tissue anchor is configured such that:

when the tissue-coupling portion of the wire is in the unconstrained state, the looped portion is shaped as an open looped portion in which the first and the second loop-end longitudinal portions do not come in mechanical contact with each other, and when the proximal end of the straight anchor-shaft portion is pulled along the anchor-shaft axis away from the looped-portion plane, the first and the second loop-end longitudinal portions come in mechanical contact with each other.

Inventive Concept 121. The tissue anchor according to Inventive Concept 118, wherein when the tissue-coupling portion of the wire is in the unconstrained state, the tail end portion generally falls in the looped-portion plane.

Inventive Concept 122. The tissue anchor according to Inventive Concept 118, wherein the tissue anchor is configured such that when the tissue-coupling portion of the wire is in the unconstrained state, the tail end portion is shaped so as to define at least one straight portion.

Inventive Concept 123. The tissue anchor according to Inventive Concept 118, wherein the tissue anchor is configured such that when the tissue-coupling portion of the wire is in the unconstrained state, the tail end portion is shaped so as to define at least one tail-end-portion curved portion.

Inventive Concept 124. The tissue anchor according to any one of Inventive Concepts 118-123, wherein the tissue anchor is configured such that when the tissue-coupling portion of the wire is in the unconstrained state, the tissue-coupling portion of the wire is shaped so as to define a first-loop-end curved portion along which the first loop-end longitudinal portion is located.

Inventive Concept 125. The tissue anchor according to Inventive Concept 124, wherein the tissue anchor is configured such that when the proximal end of the straight anchor-shaft portion is pulled along the anchor-shaft axis away from the looped-portion plane, the wire, at the second loop-end longitudinal portion, snaps into the first loop-end longitudinal portion at the first-loop-end curved portion of the wire.

Inventive Concept 126. The tissue anchor according to Inventive Concept 124, wherein the tissue anchor is configured such that when the tissue-coupling portion of the wire is in the unconstrained state, an inner curved surface of the first-loop-end curved portion has a radius of curvature equal to between 80% and 120% of a radius of the wire along the second loop-end longitudinal portion.

Inventive Concept 127. The tissue anchor according to Inventive Concept 124, wherein the first-loop-end curved portion extends directly from the distal end of the straight anchor-shaft portion.

Inventive Concept 128. The tissue anchor according to any one of Inventive Concepts 118-123, further including a fabric that covers a portion of the wire including the first loop-end longitudinal portion or the second loop-end longitudinal portion.

Inventive Concept 129. The tissue anchor according to any one of Inventive Concepts 118-123, wherein the tissue anchor is configured such that when the tissue-coupling portion of the wire is in the unconstrained state, the looped portion includes exactly one turn.

Inventive Concept 130. The tissue anchor according to any one of Inventive Concepts 118-123, further including an anchor head that is coupled to and supports the straight anchor-shaft portion of the wire.

Inventive Concept 131. A system including the tissue anchor according to any one of Inventive Concepts 118-123, wherein the system further comprises a tether coupled to the tissue anchor.

The present invention will be more fully understood from the following detailed description of embodiments thereof, taken together with the drawings, in which:

BRIEF DESCRIPTION OF THE DRAWINGS

FIG. 2A is a schematic illustration of another tissue anchor that is configured to be anchored to a cardiac tissue wall, in accordance with an application of the present invention;

FIG. 2B is a schematic illustration of a metal wire of the tissue anchor of FIG. 2A, in accordance with an application of the present invention;

FIG. 3A is a schematic illustration of yet another tissue anchor that is configured to be anchored to a cardiac tissue wall, in accordance with an application of the present invention;

FIG. 3B is a schematic illustration of a metal wire of the tissue anchor of FIG. 3A, in accordance with an application of the present invention;

FIG. 3C is a schematic illustration of another tissue anchor that is configured to be anchored to a cardiac tissue wall, in accordance with an application of the present invention;

FIG. 4A is a schematic illustration of still tissue anchor that is configured to be anchored to a cardiac tissue wall, in accordance with an application of the present invention;

FIG. 4B is a schematic illustration of a metal wire of the tissue anchor of FIG. 4A, in accordance with an application of the present invention;

FIG. 7 is a schematic illustration of a metal wire of another tissue anchor that is configured to be anchored to a cardiac tissue wall, in accordance with an application of the present invention;

FIGS. 9A and 9B are schematic illustrations of additional tissue anchors, respectively, that are configured to be anchored to a cardiac tissue wall, in accordance with respective applications of the present invention; and FIG. 10 is a schematic illustration of another tissue anchor that is configured to be anchored to a cardiac tissue wall, in accordance with an application of the present invention.

DETAILED DESCRIPTION OF APPLICATIONS

Figure 1A:
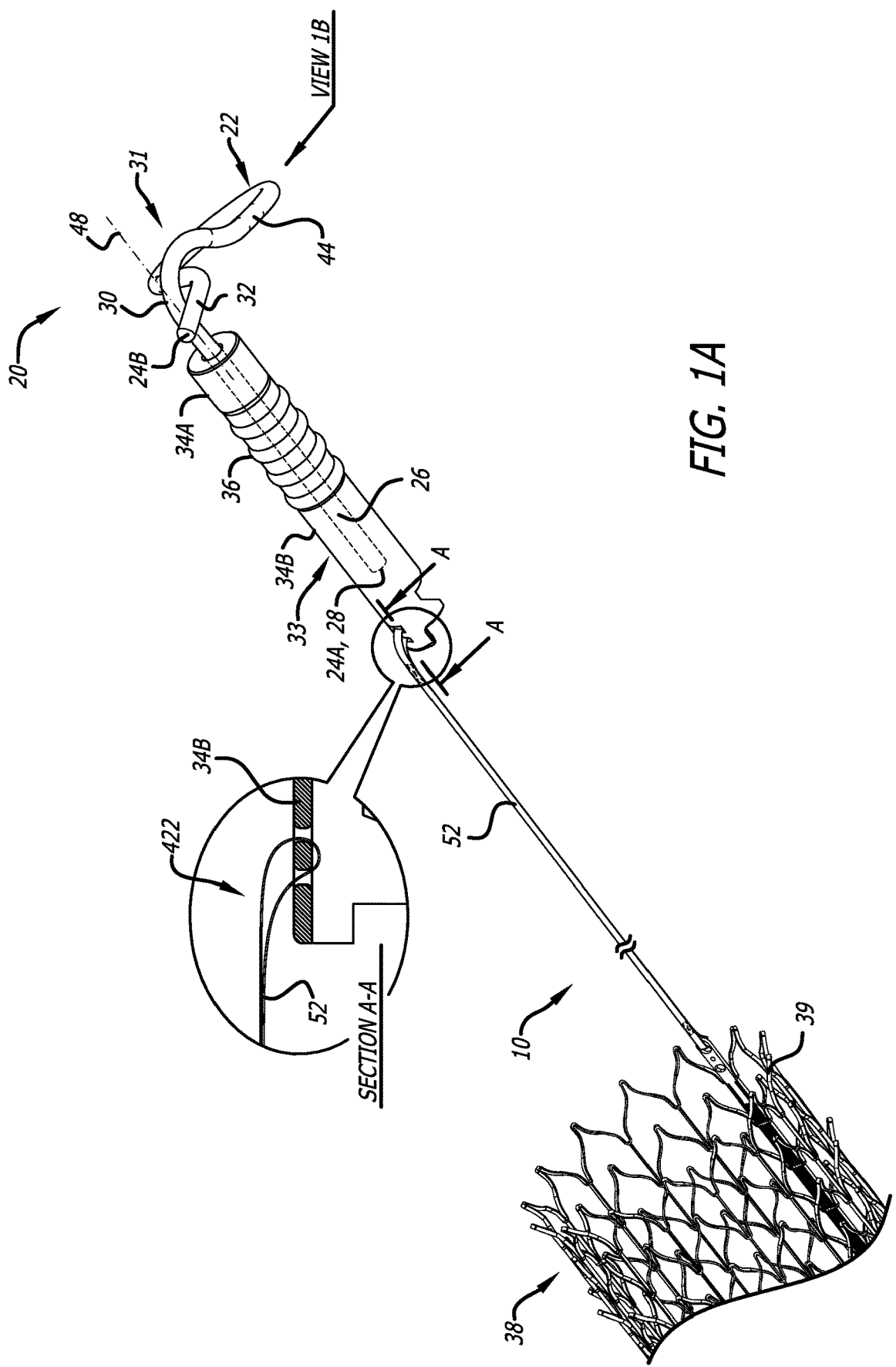
FIG. 1A is a schematic illustration of a tissue anchor that is configured to be anchored to a cardiac tissue wall, in accordance with an application of the present invention.

FIG. 1A is a schematic illustration of a tissue anchor 20 that is configured to be anchored to a cardiac tissue wall, in accordance with an application of the present invention. Tissue anchor 20 comprises a metal wire 22 that has exactly two wire ends: a first wire end 24A and a second wire end 24B. Wire 22 is shaped so as to define:

a straight anchor-shaft portion 26, which has (i) a proximal end 28 and (ii) a distal end 30, and
a tissue-coupling portion 31, which extends from distal end 30 of straight anchor-shaft portion 26, such that straight anchor-shaft portion 26 is disposed along wire 22 between tissue-coupling portion 31 and first wire end 24A.

Typically, tissue anchor 20 further comprises an anchor head 33 that is coupled to and supports straight anchor-shaft portion 26. Optionally, anchor head 33 comprises one or more collars 34, such as distal and proximal collars 34A and 34B, as shown. Alternatively, anchor head 33 comprises only a single collar 34 or does not comprise any collars 34. Optionally, anchor head 33 further comprises a sealing element 36, which is sized and shaped to be inserted with anchor head 33 into an incision through the cardiac tissue wall. Sealing element 36, along with at least a portion of anchor head 33, remains in the incision upon completion of the implantation of expandable tissue anchor 20. Sealing element 36 is configured to promote hemostasis to provide sealing of the incision. For some applications, sealing element 36 comprises a metal or a polymer, such as a bioabsorbable polymer, which breaks down after healing and hemostasis occur. For some applications, sealing element 36 implements techniques described in PCT Publication WO 2019/089262 and/or U.S. Provisional Application 62/628, 457, filed Feb. 9, 2018, both of which are assigned to the assignee of the present application and are incorporated herein by reference.

For some applications, such as shown in FIG. 1A (and in some of the other figures), proximal end 28 of straight anchor-shaft portion 26 is at first wire end 24A. Alternatively, proximal end 28 of straight anchor-shaft portion 26 does not coincide with first wire end 24A, such as described hereinbelow with reference to FIG. 3C regarding tissue anchor 270, mutatis mutandis.

Figure 1B:
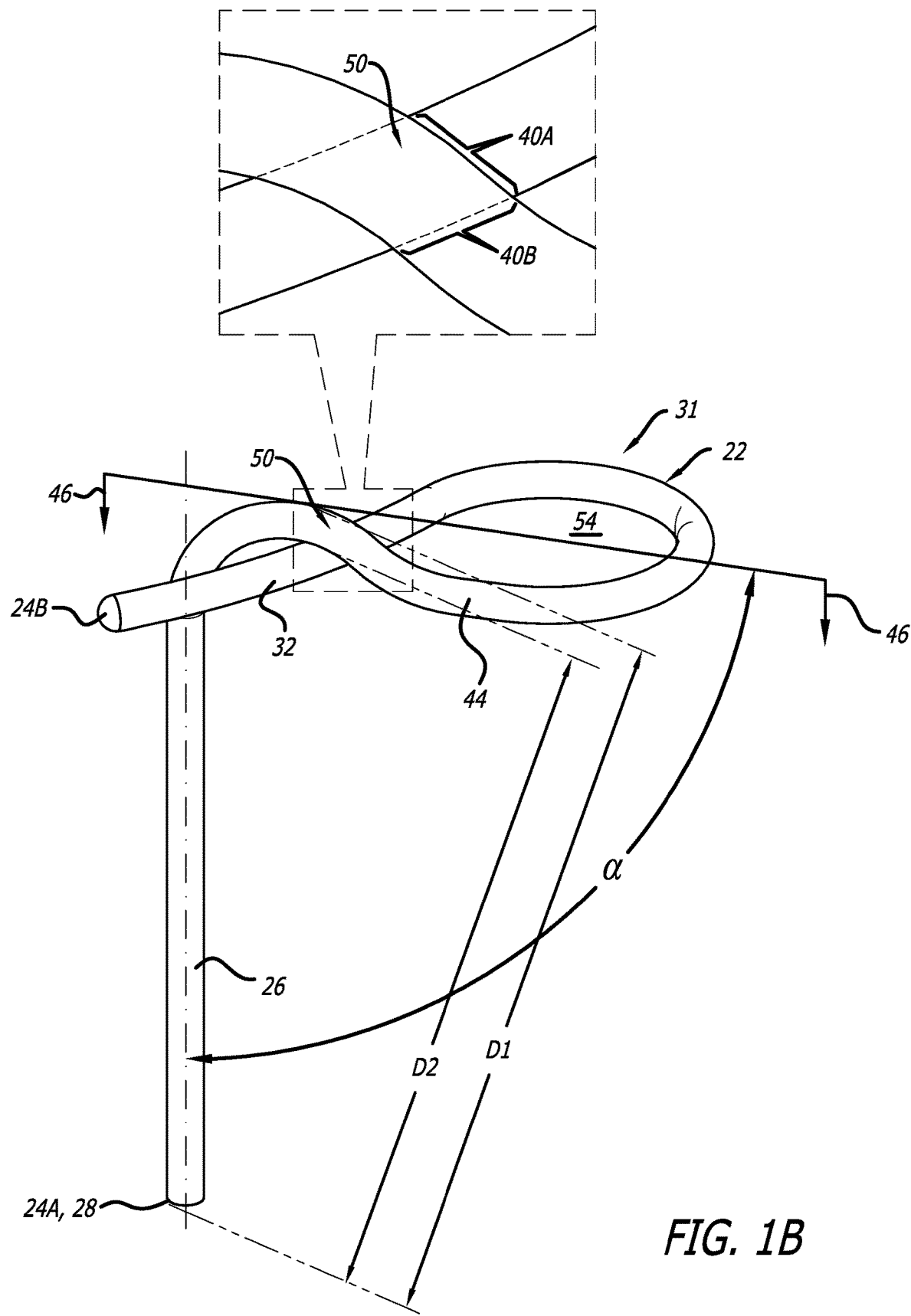
FIGS. 1B-C are schematic illustrations of two views of a metal wire of the tissue anchor of FIG. 1A, in accordance with an application of the present invention.
Figure 1C:
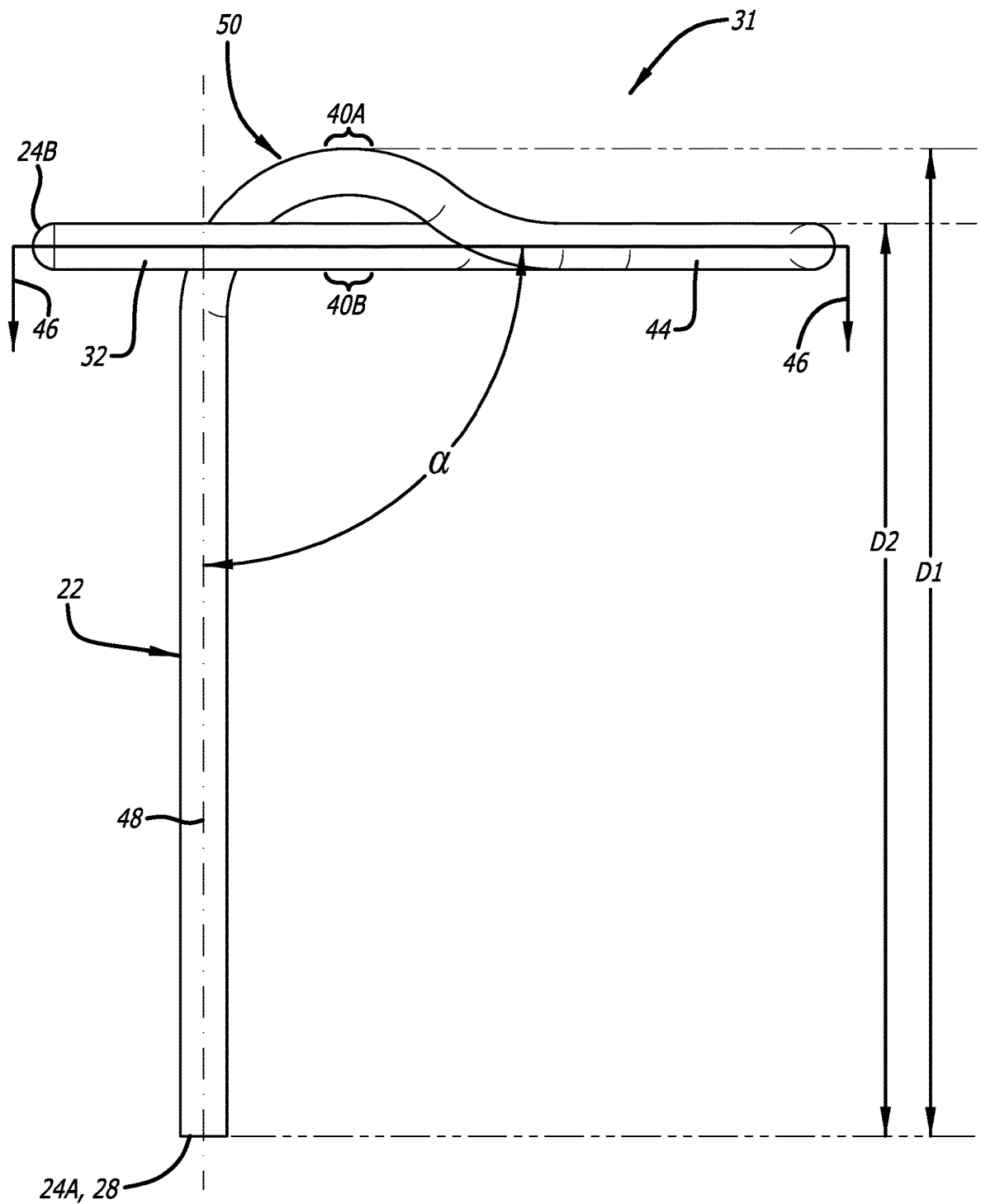

Reference is still made to FIG. 1A and is additionally made to FIGS. 1B-C, which are schematic illustrations of two views of wire 22, in accordance with an application of the present invention. Although wire 22 is typically coupled to anchor head 25, as described above, for clarity of illustration anchor head 25 is not shown in FIGS. 1B-C. FIGS. 1A-C (and FIG. 1D, described hereinbelow) show tissue-coupling portion 31 in an unconstrained state in which tissue-coupling portion 31 is not constrained by any external forces. (It is noted that straight anchor-shaft portion 26 may be configured to be straight only because it is constrained by anchor head 33, or, alternatively, even if it were not constrained by anchor head 33.)

Tissue anchor 20 is configured such that when tissue-coupling portion 31 is in the unconstrained state, such as shown in FIGS. 1A-C:

tissue-coupling portion 31 of wire 22 is shaped so as to define a tail end portion 32 that includes second wire end 24B, tissue-coupling portion 31 of wire 22 crosses itself at first and second loop-end longitudinal portions 40A and 40B along wire 22, so as to define a looped portion 44, which generally defines a looped-portion plane 46 that forms an angle α (alpha) of between 75 and 90 degrees (e.g., 90 degrees) with an anchor-shaft axis 48 of straight anchor-shaft portion 26, first loop-end longitudinal portion 40A is closer to first wire end 24A (and thus typically to proximal end 28 of straight anchor-shaft portion 26) along wire 22 than second loop-end longitudinal portion 40B is to first wire end 24A along wire 22 (and thus typically to proximal end 28 of straight anchor-shaft portion 26), and a greatest absolute distance D1 between first loop-end longitudinal portion 40A and first wire end 24A is greater than a greatest absolute distance D2 between second loop-end longitudinal portion 40B and first wire end 24A (thus, in addition, typically a greatest absolute distance between first loop-end longitudinal portion 40A and proximal end 28 of straight anchor-shaft portion 26 is greater than a greatest absolute distance between second loop-end longitudinal portion 40B and proximal end 28 of straight anchor-shaft portion 26).

As described hereinbelow with reference to FIG. 8, tissue anchor 20 is delivered to a cardiac chamber within a deployment tool. Tissue-coupling portion 31 is delivered in an unexpanded generally elongate configuration within the deployment tool, through the cardiac tissue wall from a first side of the wall to a second side of the wall, such as described hereinbelow with reference to FIG. 8. Tissue-coupling portion 31 is further configured, upon deployment, to expand on the second side of the cardiac tissue wall, such as described hereinbelow with reference to FIG. 8.

Tissue anchor 20 is configured such that when proximal end 28 of straight anchor-shaft portion 26 is pulled along anchor-shaft axis 48 away from looped-portion plane 46, mechanical contact between first and second loop-end longitudinal portions 40A and 40B locks looped portion 44 and prevents looped portion 44 from straightening as a result of the applied tension. Typically, the above-mentioned pulling is performed using tether 52 coupled to tissue anchor 20, such as to anchor head 33, as described hereinbelow. (The mechanical contact between first and second loop-end longitudinal portions 40A and 40B may either be direct, or via a coating or fabric 560 described hereinbelow with reference to FIGS. 6A-B.)

Typically, tissue anchor 20 is configured such that when tissue-coupling portion 31 of wire 22 is in the unconstrained state, anchor-shaft axis 48 does not pass through a space 54 surrounded by and defined by looped portion 44, such as shown in FIGS. 1A-C.

Typically, tissue anchor 20 is configured such that when tissue-coupling portion 31 of wire 22 is in the unconstrained state, looped portion 44 includes exactly one turn, such as shown in FIGS. 1A-C. Alternatively, looped portion 44 includes more than one turn (configuration not shown).

For some applications, tissue anchor 20 is configured such that when tissue-coupling portion 31 of wire 22 is in the unconstrained state, wire 22 crosses itself exactly once, at first and second loop-end longitudinal portions 40A and 40B along wire 22.

For some applications, tissue anchor 20 is configured such that when tissue-coupling portion 31 of wire 22 is in the unconstrained state, wire 22 defines only a single looped portion 44.

For some applications, when tissue-coupling portion 31 of wire 22 is in the unconstrained state, tail end portion 32 generally falls in looped-portion plane 46, such as shown in FIGS. 1A-C, and thus may aid with anchoring.

For some applications, when tissue-coupling portion 31 of wire 22 is in the unconstrained state, no portion of tail end portion 32 is parallel to straight anchor-shaft portion 26.

For some applications, such as shown in FIGS. 1A-C, tissue anchor 20 is configured such that when tissue-coupling portion 31 of wire 22 is in the unconstrained state, wire 22 is shaped so as to define a first-loop-end curved portion 50 along which first loop-end longitudinal portion 40A is located. Alternatively, tissue anchor 20 is configured such that when tissue-coupling portion 31 of wire 22 is in the unconstrained state, wire 22 is shaped so as to define a first-loop-end straight portion along which first loop-end longitudinal portion 40A is located (such as metal wire 622, described hereinbelow with reference to FIG. 7); in this case wire 22 may optionally be shaped so as to define a second-loop-end curved portion along which second loop-end longitudinal portion 40B is located (configuration not shown), or wire 22 may not be shaped so as to define a second-loop-end curved portion (such as metal wire 622, described hereinbelow with reference to FIG. 7).

For some applications, wire 22 is not shaped so as to define any looped portions proximal to proximal end 28 of straight anchor-shaft portion 26.

For some applications, a system 10 is provided that comprises tissue anchor 20 and a tether 52 affixed to tissue anchor 20, such as to anchor head 33, e.g., to distal collar 34A of anchor head 33. Thus, tether 52 is typically indirectly coupled to straight anchor-shaft portion 26 via anchor head 33. For some applications, system 10 further comprises a second tissue anchor 38 separate and distinct from tissue anchor 20. Typically, second tissue anchor 38 is couplable to, or coupled to, tissue anchor 20 by tether 52. For some applications, second tissue anchor 38 comprises a stent 39, as shown. Alternatively, second tissue anchor 38 comprises another type of tissue anchor, such as a helical tissue anchor, as known in the art; another tissue anchor identical or similar to tissue anchor 20; a tissue anchor known in the art; or any of the tissue anchors described in the patent application publications and/or patents incorporated hereinbelow by reference.

For some applications, when tissue-coupling portion 31 of wire 22 is in the unconstrained state, looped portion 44 is shaped as an open looped portion in which first and second loop-end longitudinal portions 40A and 40B are not in mechanical contact with each other (either directly, or via a coating or fabric 560 described hereinbelow with reference to FIGS. 6A-B). (In these applications, looped portion 44 is considered "an open looped portion" in the sense that wire 22 curves back toward itself and crosses itself to define space 54, even though first and second loop-end longitudinal portions 40A and 40B are not in mechanical contact with each other.) For these applications, tissue anchor 20 is configured such that when proximal end 28 of straight anchor-shaft portion 26 is pulled along anchor-shaft axis 48 away from looped-portion plane 46, first and second loop-end longitudinal portions 40A and 40B come in mechanical contact with each other (either directly, or via a coating or fabric 560 described hereinbelow with reference to FIGS. 6A-B).

For other applications, when tissue-coupling portion 31 of wire 22 is in the unconstrained state (i.e., even before proximal end 28 of straight anchor-shaft portion 26 is pulled along anchor-shaft axis 48 away from looped-portion plane 46), looped portion 44 is shaped as a closed looped portion in which first and second loop-end longitudinal portions 40A and 40B are in mechanical contact with each other (either directly, or via a coating or fabric 560 described hereinbelow with reference to FIGS. 6A-B).

As used in the present application, including in the claims, the term "looped portion" includes within its scope both an open looped portion and a closed loop portion.

Figure 1D:
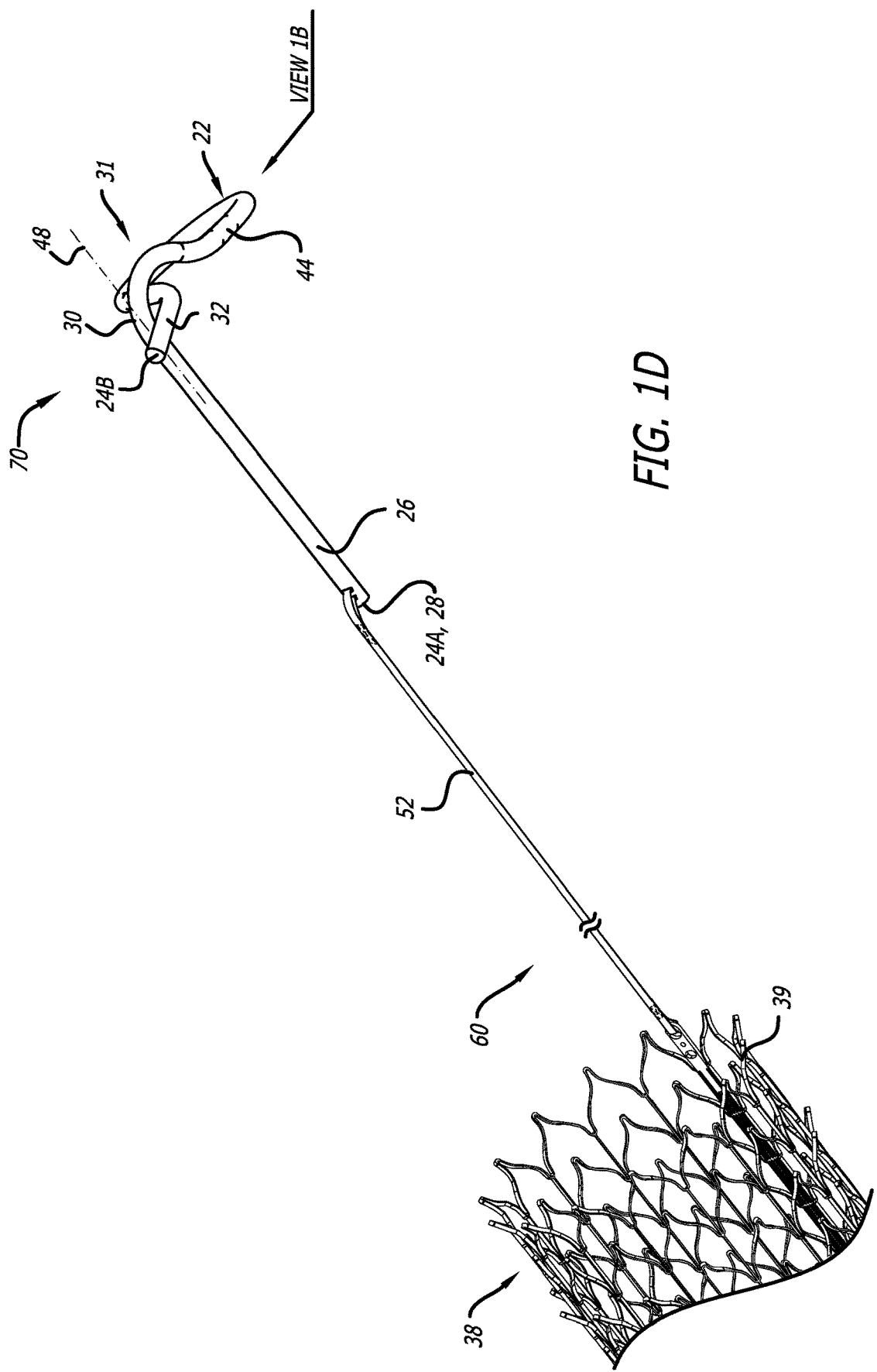
FIG. 1D is a schematic illustration of a system comprising a tissue anchor and a tether, in accordance with an application of the present invention.

Reference is now made to FIG. 1D, which is a schematic illustration of a system 60 comprising a tissue anchor 70 and tether 52, in accordance with an application of the present invention. Except as described below, system 60 is identical to system 10 and tissue anchor 70 is identical to tissue anchor 20 described hereinabove with reference to FIGS. 1A-C, and like reference numerals refer to like parts.

Unlike in tissue anchor 20, described hereinabove with reference to FIG. 1A, tether 52 is coupled to tissue anchor 70 by being coupled directly to straight anchor-shaft portion 26. Tissue anchor 70 does not comprise anchor head 33. Thus, tether 52 is typically directly coupled to straight anchor-shaft portion 26. For some applications, like system 60, system 10 further comprises second tissue anchor 38 separate and distinct from tissue anchor 70. Typically, second tissue anchor 38 is couplable to, or coupled to, tissue anchor 70 by tether 52.

Reference is now made to FIG. 2A, which is a schematic illustration of a tissue anchor 120 that is configured to be anchored to a cardiac tissue wall, in accordance with an application of the present invention. Reference is also made to FIG. 2B, which is a schematic illustration of a metal wire 122 of tissue anchor 120, in accordance with an application of the present invention. Except as described below, tissue anchor 120 is identical to tissue anchor 20 described hereinabove with reference to FIGS. 1A-C, and like reference numerals refer to like parts. Tissue anchor 120 may also implement the features of tissue anchor 70, described hereinabove with reference to FIG. 1D.

When a tissue-coupling portion 131 of wire 122 is in the unconstrained state, a tail end portion 132 of tissue-coupling portion 131 of wire 122 is shaped so as to define at least one first-loop-end curved portion 154. For some applications, a distance between anchor-shaft axis 48 and a point on first-loop-end curved portion 154 farthest from anchor-shaft axis 48 equals between 40% and 150%, such as between 60% and 100%, of a distance between anchor-shaft axis 48 and a point on looped portion 44 farthest from anchor-shaft axis 48. This arrangement may add balance to the anchoring provided by tissue anchor 120.

Reference is now made to FIG. 3A, which is a schematic illustration of a tissue anchor 220 that is configured to be anchored to a cardiac tissue wall, in accordance with an application of the present invention. Reference is also made to FIG. 3B, which is a schematic illustration of a metal wire 222 of tissue anchor 220, in accordance with an application of the present invention. Except as described below, tissue anchor 220 is identical to tissue anchor 20 described hereinabove with reference to FIGS. 1A-C, and like reference numerals refer to like parts. Tissue anchor 220 may also implement the features of tissue anchor 70, described hereinabove with reference to FIG. 1D.

When tissue-coupling portion 231 of wire 222 is in the unconstrained state, a tail end portion 232 of tissue-coupling portion 231 of wire 222 is shaped so as to define at least one straight portion 256. Straight portion 256 typically extends to second wire end 24B. For some applications, a distance between anchor-shaft axis 48 and a point on straight portion 256 (e.g., second wire end 24B) farthest from anchor-shaft axis 48 equals between 40% and 150%, such as between 60% and 100%, of a distance between anchor-shaft axis 48 and a point on looped portion 44 farthest from anchor-shaft axis 48. This arrangement may add balance to the anchoring provided by tissue anchor 220.

Reference is now made to FIG. 3C, which is a schematic illustration of a tissue anchor 270 that is configured to be anchored to a cardiac tissue wall, in accordance with an application of the present invention. Except as described below, tissue anchor 270 is identical to tissue anchor 220, described hereinabove with reference to FIGS. 3A-B, and like reference numerals refer to like parts. Any of the tissue anchors described herein may implement the features of tissue anchor 270, mutatis mutandis.

In this configuration, proximal end 28 of a straight anchor-shaft portion 276 of wire 222 of tissue anchor 270 does not coincide with first wire end 24A; instead, first wire end 24A is proximal to proximal end 28 of straight anchor-shaft portion 276 along wire 222. For example, wire 222 may be at least partially curved between first wire end 24A and proximal end 28 of straight anchor-shaft portion 276 (e.g., bent away from anchor-shaft axis 48), as shown in FIG. 3C, and/or may define one or more sharp angles between first wire end 24A and proximal end 28 of straight anchor-shaft portion 276 (configuration not shown).

Reference is now made to FIG. 4A, which is a schematic illustration of a tissue anchor 320 that is configured to be anchored to a cardiac tissue wall, in accordance with an application of the present invention. Reference is also made to FIG. 4B, which is a schematic illustration of a metal wire 322 of tissue anchor 320, in accordance with an application of the present invention. Except as described below, tissue anchor 320 is identical to tissue anchor 20 described hereinabove with reference to FIGS. 1A-C, and like reference numerals refer to like parts. Tissue anchor 320 may also implement the features of tissue anchor 70, described hereinabove with reference to FIG. 1D.

When tissue-coupling portion 331 of wire 322 is in the unconstrained state, such as shown in FIGS. 4A-B:
- tissue-coupling portion 331 of wire 322 is shaped so as to define a tail end portion 332 that includes second wire end 24B,
- tissue-coupling portion 331 of wire 322 crosses itself at first and second loop-end longitudinal portions 340A and 340B along wire 322, so as to define a looped portion 344, which generally defines a looped-portion plane 346 that forms an angle of between 75 and 90 degrees (e.g., 90 degrees) with anchor-shaft axis 48 of straight anchor-shaft portion 26,
- first loop-end longitudinal portion 340A is closer to first wire end 24A along wire 322 than second loop-end longitudinal portion 340B is to first wire end 24A along wire 322, and
- a greatest absolute distance D1 between first loop-end longitudinal portion 340A and first wire end 24A is greater than a greatest absolute distance D2 between second loop-end longitudinal portion 340B and first wire end 24A.

When tissue-coupling portion 331 of wire 322 is in the unconstrained state, wire 322 is shaped so as to define a first-loop-end curved portion 350 along which first loop-end longitudinal portion 340A is located. Tissue anchor 320 is configured such that when proximal end 28 of straight anchor-shaft portion 26 is pulled along anchor-shaft axis 48 away from looped-portion plane 46, wire 322, at second loop-end longitudinal portion 340B, snaps into first loop-end longitudinal portion 340A at first-loop-end curved portion 350 of wire 22. This snapping locks looped portion 344 and prevents straightening of looped portion 344.

For some applications, tissue anchor 320 is configured such that when tissue-coupling portion 331 of wire 322 is in the unconstrained state, an inner curved surface 358 of first-loop-end curved portion 350 has a radius of curvature $r_C$ equal to between 80% and 120% (e.g., between 90% and 110%, such as 100%) of a radius of wire 322 along second loop-end longitudinal portion 340B. For some applications, first-loop-end curved portion 350 extends directly from distal end 30 of straight anchor-shaft portion 26.

Figure 5B:
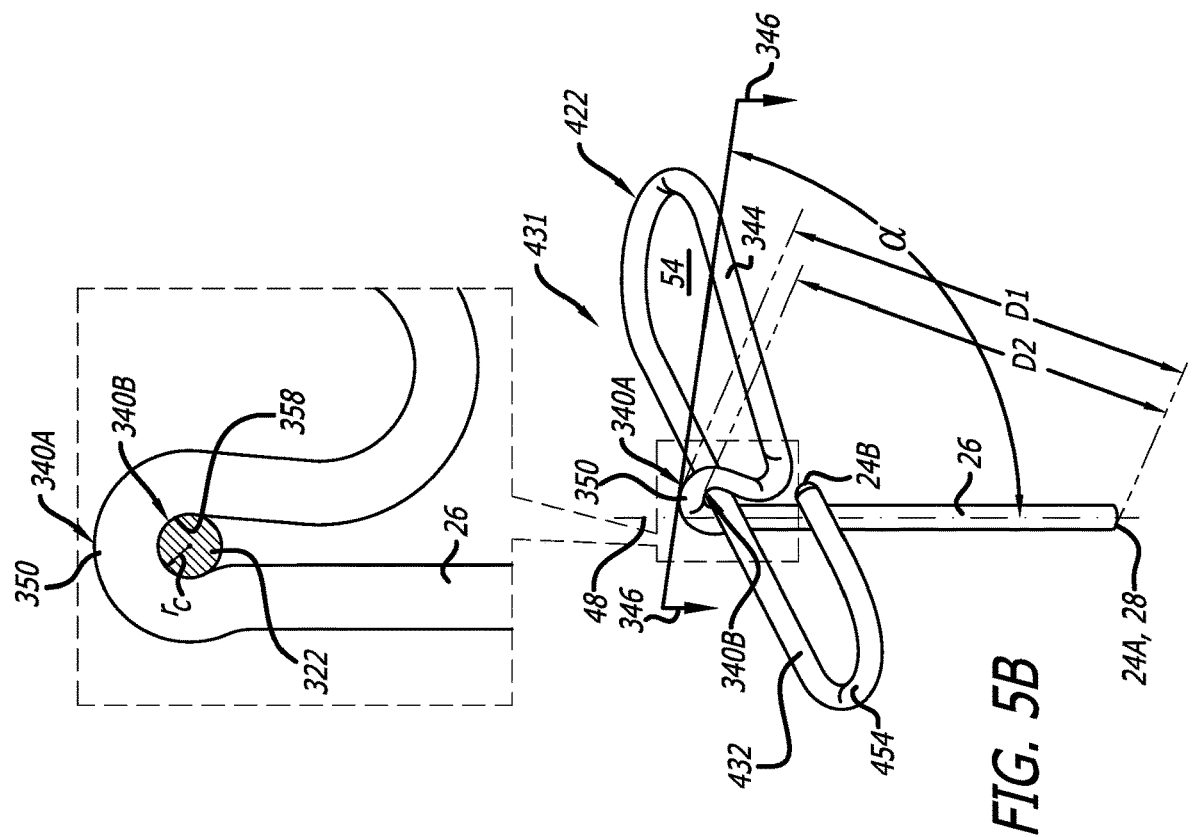
FIG. 5B is a schematic illustration of a metal wire of the tissue anchor of FIG. 5A, in accordance with an application of the present invention.
Figure 5A:
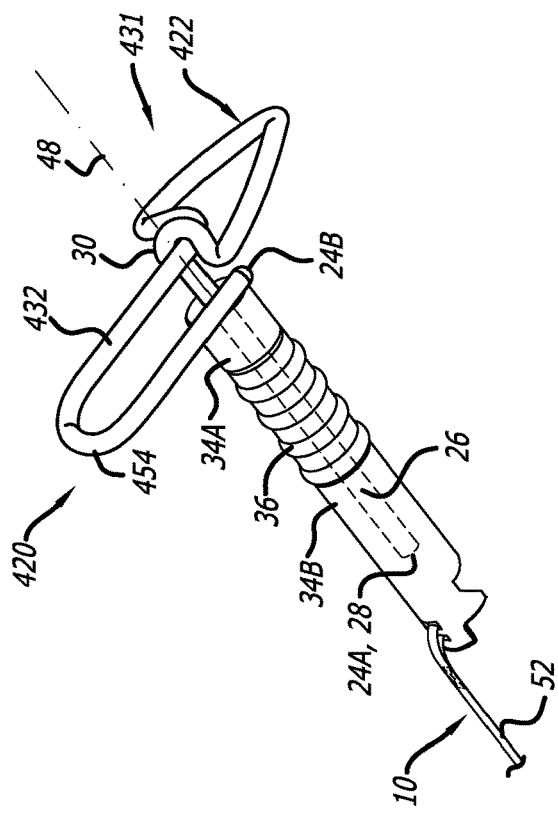
FIG. 5A is a schematic illustration of another tissue anchor that is configured to be anchored to a cardiac tissue wall, in accordance with an application of the present invention.

Typically, when wire 322 is snapped into first loop-end longitudinal portion 340A at first-loop-end curved portion 350 of wire 322, inner curved surface 358 of first-loop-end curved portion 350 surrounds at least 180 degrees of wire 322 at first loop-end longitudinal portion 340A. For example, inner curved surface 358 may surround 180 degrees, or slightly more, such as shown in FIGS. 4A-B, or at least 200 degrees, such as shown in FIGS. 5A-B, described hereinbelow. The configurations illustrated in FIGS. 4A-B, 5A-B, and 6A-B may implement the lesser degree of surrounding shown in FIGS. 4A-B and 6A-B or the greater degree of surrounding shown in FIGS. 5A-B.

For some applications, when tissue-coupling portion 331 of wire 322 is in the unconstrained state, tail end portion 332 is shaped so as to define at least one straight portion 356. Straight portion 356 typically extends to second wire end 24B.

Reference is now made to FIG. 5A, which is a schematic illustration of a tissue anchor 420 that is configured to be anchored to a cardiac tissue wall, in accordance with an application of the present invention. Reference is also made to FIG. 5B, which is a schematic illustration of a metal wire 422 of tissue anchor 420, in accordance with an application of the present invention. Except as described below, tissue anchor 420 is identical to tissue anchor 320 described hereinabove with reference to FIGS. 4A-B, and like reference numerals refer to like parts. Tissue anchor 420 may also implement the features of tissue anchor 70, described hereinabove with reference to FIG. 1D.

When a tissue-coupling portion 431 of wire 422 is in the unconstrained state, a tail end portion 432 of tissue-coupling portion 431 of wire 422 is shaped so as to define at least one tail-end-portion curved portion 454.

Figure 6A:
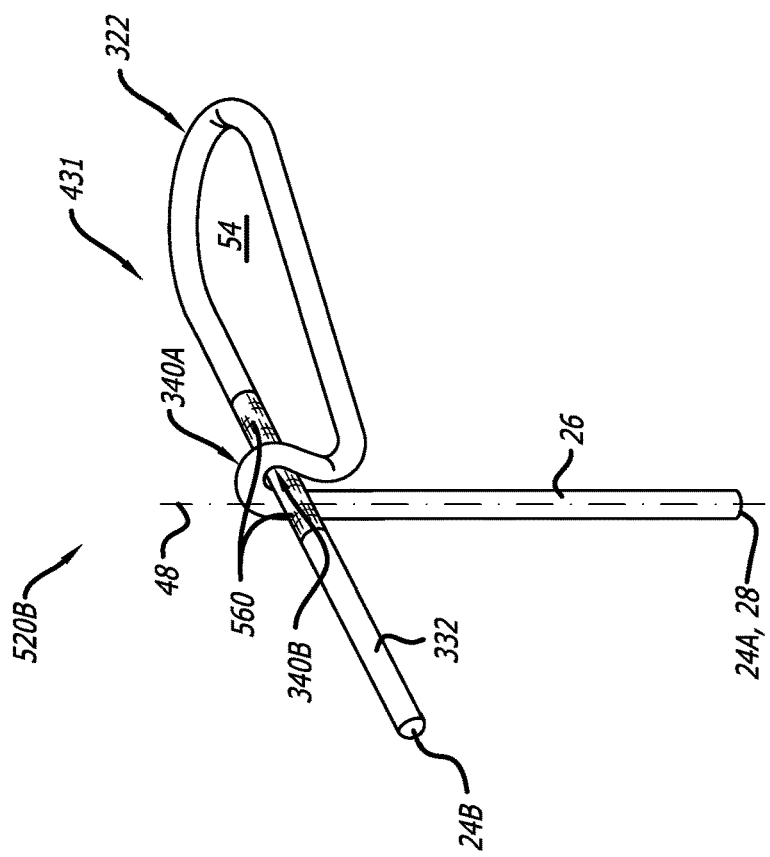
FIGS. 6A and 6B are schematic illustrations of metal wires of tissue anchors that are configured to be anchored to a cardiac tissue wall, in accordance with respective applications of the present invention.
Figure 6B:
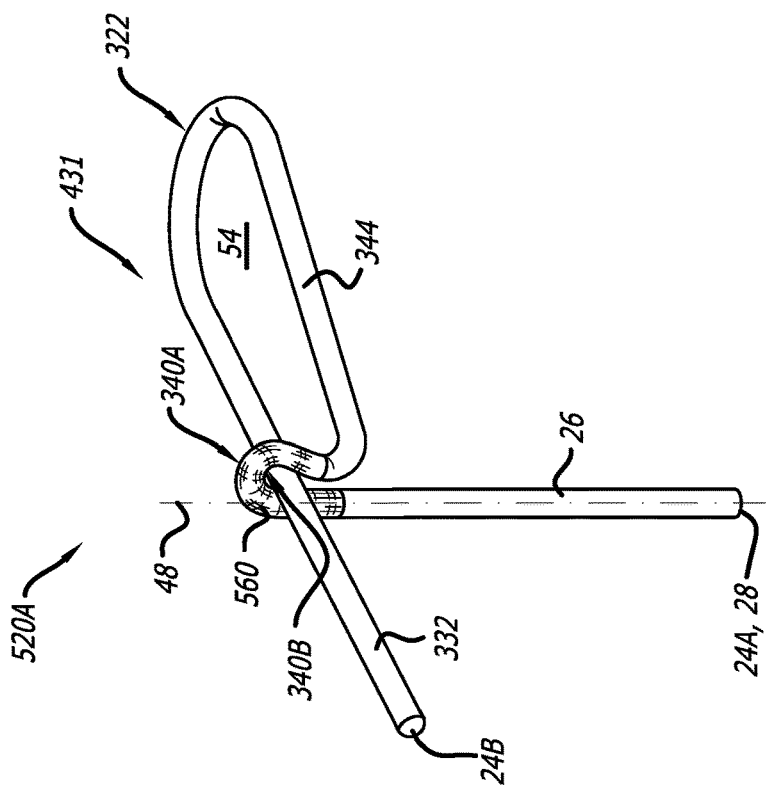

Reference is now made to FIGS. 6A and 6B, which are schematic illustrations of metal wires 322 of tissue anchors 520A and 520B, respectively, that are configured to be anchored to a cardiac tissue wall, in accordance with respective applications of the present invention. Except as described below, tissue anchors 520A and 520B are identical to tissue anchor 320 described hereinabove with reference to FIGS. 4A-B, and like reference numerals refer to like parts. The features of tissue anchors 520A and 520B may also be implemented in combination with the other tissue anchors described herein, mutatis mutandis.

Tissue anchors 520A and 520B further comprise a fabric 560 that covers a portion of metal wire 322 including first loop-end longitudinal portion 340A (tissue anchor 520A, shown in FIG. 6A) or second loop-end longitudinal portion 340B (tissue anchor 520B, shown in FIG. 6B). Fabric 560 may help prevent erosion of the metal of wire 322 in the event that second loop-end longitudinal portion 340B moves back and forth with respect to first-loop-end curved portion 350 (e.g., in a crook defined by first-loop-end curved portion 350).

Reference is now made to FIG. 7, which is a schematic illustration of a metal wire 622 of a tissue anchor 620 that is configured to be anchored to a cardiac tissue wall, in accordance with an application of the present invention. Except as described below, tissue anchor 620 is identical to tissue anchor 20 described hereinabove with reference to FIGS. 1A-C, and like reference numerals refer to like parts. Tissue anchor 620 may also implement the features of tissue anchor 70, described hereinabove with reference to FIG. 1D, or any of the other tissue anchors described herein, mutatis mutandis; for example, tissue anchor 620 may comprise anchor head 33. Although a tail end portion 432 of a tissue-coupling portion 631 of wire 622 is shown as being shaped so as to define at least one tail-end-portion curved portion 454, alternatively tail end portion 432 does not define any tail-end-portion curved portions, such as shown in FIGS. 1A-D, 3A-C, 4A-B, and 6A-B.

Tissue anchor 620 is configured such that a tissue-coupling portion 631 of wire 622 is in the unconstrained state, (a) a tissue-coupling portion 631 of wire 622 crosses itself at first and second loop-end longitudinal portions 640A and 640B along wire 622, so as to define a looped portion 644, and (b) tissue-coupling portion 631 is shaped so as to define:
  a first-loop-end straight portion 623A along which a first loop-end longitudinal portion 640A is located, and/or
  a second-loop-end straight portion 623B along which a second loop-end longitudinal portion 640B is located.

It is noted that wire 622 of looped portion 644 is shown in FIG. 7 as looping from first-loop-end straight portion 623A to second-loop-end straight portion 623B in a clockwise direction, as viewed from above the looped-portion plane (i.e., from the side of the looped-portion plane opposite first wire end 24A). Wire 622 may also loop in a counterclockwise direction. Similarly, the wires of the looped portions of the tissue anchors shown in FIGS. 1A-D, 2A-B, 3A-C, 4A-B, 5A-B, and 6A-B are shown as looping from the first-loop-end straight portion to the second-loop-end straight portion in a counterclockwise direction, as viewed from above the looped-portion planes; these wires may also loop in a clockwise direction.

Figure 8:
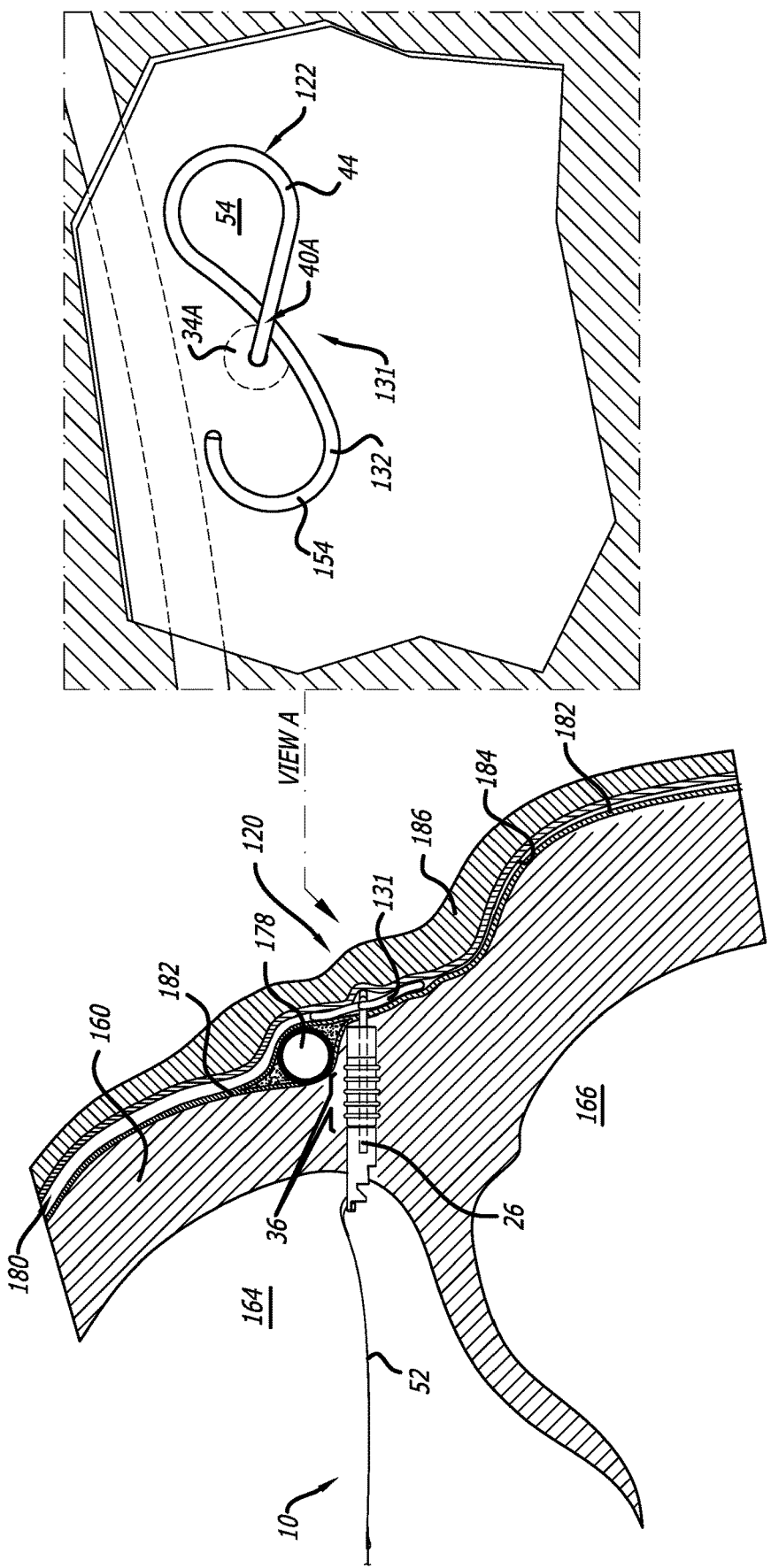
FIG. 8 is a schematic illustration of a method of deploying the tissue anchor of FIGS. 2A-B through a myocardial tissue wall, in accordance with an application of the present invention.

Reference is now made to FIG. 8, which is a schematic illustration of a method of deploying tissue anchor 120 through a myocardial tissue wall 160, in accordance with an application of the present invention. Although in FIG. 8 tissue anchor 120 is shown deployed through a myocardial tissue wall, tissue anchor 120 may also be deployed through other cardiac tissue walls, such as the interatrial septum, either at or not at the fossa ovalis, or through other non-cardiac tissue walls. Indeed, the tissue anchors described herein may be deployed in any number of bodily locations where it is desired to anchor into or behind tissue for purposes of moving such tissue relative to adjacent tissue. Although FIG. 8 shows the deployment of tissue anchor 120, the other tissue anchors described herein may be similarly deployed.

Tissue anchor 120 is delivered to a target site, such as a cardiac chamber, within a deployment tool, with tissue-coupling portion 131 in an unexpanded generally elongate configuration within the deployment tool. The deployment tool may comprise a hollow needle. The cardiac chamber may be a right atrium 164 (as shown), a right ventricle 166 (configuration not shown), a left atrium (configuration not shown), or a left ventricle (configuration not shown). Tissue-coupling portion 131 of wire 122 is delivered in the unexpanded generally elongate configuration through a cardiac tissue wall from a first side of the cardiac tissue wall to a second farther side of the cardiac tissue wall. In one application, the hollow needle is used to puncture through a first side of a myocardial tissue wall 160 and visceral pericardium 182 (which is part of the epicardium), avoiding vasculature such as the right coronary artery (RCA) 178. For some applications, the deployment tool is then further directed, beyond the second farther side of the cardiac tissue wall, into the pericardial cavity 180 between visceral pericardium 182 and parietal pericardium 184, carefully avoiding puncturing parietal pericardium 184 and fibrous pericardium 186. Although the performance of these steps of the method is not shown in FIG. 8, these steps may be performed using techniques described in PCT Publication WO 2018/035378 to Tobis et al., which is incorporated herein by reference, with reference to FIGS. 6A-C thereof.

As shown in FIG. 8, tissue anchor 120 is released from the deployment tool such that straight anchor-shaft portion 26 of wire 122 is disposed at least partially within the cardiac tissue wall, and tissue-coupling portion 131 of wire 122 expands outside the second farther side of the cardiac tissue wall (optionally within pericardial cavity 180, as shown in FIG. 8), and assumes the shape described hereinabove, thereby anchoring tissue anchor 120 to myocardial tissue wall 160.

Once tissue anchor 120 has been anchored to myocardial tissue wall 160 at the target site, expanded tissue-coupling portion 131, including looped portion 44 thereof, is tightly drawn against the second farther side of myocardial tissue wall 160 (typically via visceral pericardium 182) at the target site by applying tension to tissue anchor 120 by pulling proximal end 28 of straight anchor-shaft portion 26 along anchor-shaft axis 48 away from looped-portion plane 46. The tension is thus applied to tissue-coupling portion 131 and thus to myocardial tissue wall 160, thereby moving myocardial tissue wall 160 at the target site relative to adjacent cardiac tissue. For some applications, such motion can have the benefit of altering the geometry of a nearby cardiac valve, such as the tricuspid valve or the mitral valve. Typically, the tension is applied using tether 52.

Reference is now made to FIGS. 9A and 9B, which are schematic illustrations of tissue anchors 720A and 720B, respectively, that are configured to be anchored to a cardiac tissue wall, in accordance with respective applications of the present invention.

Reference is also made to FIG. 10, which is a schematic illustration of a tissue anchor 820 that is configured to be anchored to a cardiac tissue wall, in accordance with an application of the present invention.

Tissue anchors 720A, 720B, and 820 comprise:
straight anchor-shaft portions 726A, 726B, and 826, respectively; and
tissue-coupling portions 731A, 731B, and 831, respectively.

Tissue anchors 720A, 720B, and 820 are configured such that when tissue-coupling portions 731A, 731B, and 831, respectively, are in respective unconstrained states in which the tissue-coupling portions are not constrained by any external forces, as shown in FIGS. 9A-B and 10:
tissue-coupling portions 731A, 731B, and 831 are shaped so as to define (i) elongate intermediate portions 735A, 735B, and 835, respectively, that extend from distal ends 730A, 730B, and 830, respectively, of straight anchor-shaft portions 726A, 726B, and 826, respectively, and (ii) forked distal portions 737A, 737B, and 837, respectively, that extend from distal ends 741A, 741B, and 841, respectively, of intermediate portions 735A, 735B, and 835, respectively, and define two tines 743A, 743B, and 843, respectively, and
tine-passing portions 745A, 745B, and 845, respectively, of tissue anchors 720A, 720B, and 820, respectively, pass between the two tines 743A, 743B, and 843, respectively.

For some applications, such as shown in FIGS. 9A and 10 for tissue anchors 720A and 820, respectively, tine-passing portions 745A and 845 are defined by straight anchor-shaft portions 726A and 826, respectively. For other applications, such as shown in FIG. 9B for tissue anchor 720B, tine-passing portion 745B is defined by intermediate portion 735B. Alternatively, the tine-passing portion is defined partially by the straight anchor-shaft portion and partially by the intermediate portion (configuration not shown). Tissue anchor 820 may alternatively be shaped such that tine-passing portion 845 is defined by intermediate portion 835, similar to the configuration shown in FIG. 9B (configuration not shown).

For some applications, each of the tissue anchors is configured such that when the tissue-coupling portion is in the unconstrained state, exactly one tine-passing portion of the tissue anchor passes between the two tines, as shown in FIGS. 9A-B and 10.

For some applications, each of the tissue anchors is configured such that when the tissue-coupling portion is in the unconstrained state, the two tines generally define a tine plane 747 that forms an angle of between 60 and 90 degrees (e.g., between 75 and 90 degrees) with an anchor-shaft axis 749 of the straight anchor-shaft portion (labeled in FIG. 9A for tissue anchor 720A, but equally applicable to tissue anchors 720B and 820).

For some applications, tissue anchors 720A, 720B, and 820 are configured such that when tissue-coupling portions 731A, 731B, and 831 are in the unconstrained states, intermediate portions 735A, 735B, and 835 are at least partially curved.

For some applications, tissue anchors 720A, 720B, and 820 further comprising a fabric that at least partially covers the tissue-coupling element, such as described, for example, regarding fabric 560 with reference to FIGS. 6A-B.

Reference is made to FIGS. 9A-B. For some applications, each of tissue anchors 720A and 720B comprises a single metal wire 722 that is shaped so as to define straight anchor-shaft portion 726A, 726B and tissue-coupling portion 731A, 731B. For some of these applications, a proximal end 728 of straight anchor-shaft portion 726A, 726B coincides with a proximal end 724 of wire 722. Alternatively, proximal end 728 of straight anchor-shaft portion 726A, 726B does not coincide with proximal end 724 of wire 722, such as described hereinabove with reference to FIG. 3C regarding tissue anchor 270, mutatis mutandis.

Reference is made to FIG. 10. For some applications, tissue anchor 820 comprises two metal wires 822A and 822B that are shaped so as to together define straight anchor-shaft portion 826 and tissue-coupling portion 831. Tissue anchor 820 is configured such that when tissue-coupling portion 831 is in the unconstrained state, as shown in FIG. 10, the two metal wires 822A and 822B:
run alongside (i.e., directly adjacent) each other along at least a portion of straight anchor-shaft portion 826 and along at least a portion of intermediate portion 835, and
are separate from each other along forked distal portion 837, such that the two wires 822A and 822B respectively define the two tines 843.

Typically, but not necessarily, the two metal wires 822A and 822B are fixed to each other at least partially along straight anchor-shaft portion 826 and at least partially along intermediate portion 835.

For some applications, a proximal end 828 of straight anchor-shaft portion 826 coincides with a proximal end 824A and/or 824B of at least one of the two wires 822A and 822B, such as with both proximal ends 724A and 724B, as shown in FIG. 10. Alternatively, proximal end 828 of straight anchor-shaft portion 826 does not coincide with proximal end 824A and/or 824B of at least one of the two wires 822A and 822B, such as described hereinabove with reference to FIG. 3C regarding tissue anchor 270, mutatis mutandis.

Reference is again made to FIGS. 9A-B and 10. For some applications, tissue anchors 720A, 720B, and 820 are configured such that:
when tissue-coupling portions 731A, 731B, and 831 are in the unconstrained states, intermediate portions 735A, 735B, and 835, respectively, are not in mechanical contact with themselves or with either of the two tines 743A, 743B, and 843, respectively (either directly, or via a coating or the above-mentioned optional fabric), and
when proximal end 728, 828 of straight anchor-shaft portion 726A, 726B, and 826, respectively, is pulled, along anchor-shaft axis 749 away from tine plane 747, intermediate portions 735A, 735B, and 835, respectively, come in mechanical contact with at least one element selected from the group consisting of: intermediate portions 735A, 735B, and 835, respectively (i.e., a different longitudinal portion of the intermediate portion) and at least one of the two tines 743A, 743B, and 843, respectively (either directly, or via a coating or the above-mentioned optional fabric).

For some of these applications, tissue anchors 720A, 720B, and 820 are configured such that when proximal end 728, 828 of straight anchor-shaft portion 726A, 726B, and 826, respectively, is pulled along anchor-shaft axis 749 away from tine plane 747, intermediate portions 735A, 735B, and 835, respectively, come in mechanical contact with tissue-coupling portions 731A, 731B, and 831, respectively, at junctions 751A, 751B, and 851, respectively, at which the tissue-coupling portion forks into the two tines.

Reference is still made to FIGS. 9A-B and 10. Typically, each of tissue anchors 720A, 720B, and 820 further comprises an anchor head that is coupled to and supports the straight anchor-shaft portion. The anchor head may implement any of the features of anchor head 33 described hereinabove with reference to FIG. 1A. Alternatively, the tissue anchors do not comprise an anchor head, such as described hereinabove regarding tissue anchor 70, with reference to FIG. 1D. A tissue anchor system may be provided that comprises one of tissue anchors 720A, 720B, and 820 and a tether, and, optionally, a second tissue anchor, such as described hereinabove with reference to FIGS. 1A and 1D.

For some applications, tissue anchors 720A, 720B, and 820 are deployed generally as described hereinabove with reference to FIG. 8 for tissue anchor 20, mutatis mutandis. The tissue anchor is delivered, to a cardiac chamber, within a deployment tool with the tissue-coupling portion is in an unexpanded generally elongate configuration. The tissue-coupling portion is delivered in the unexpanded generally elongate configuration through a cardiac tissue wall from a first side of the cardiac tissue wall to a second farther side of the cardiac tissue wall. The tissue anchor is released from the deployment tool such that the straight anchor-shaft portion of the wire is disposed at least partially within the cardiac tissue wall, the tissue-coupling portion is disposed outside the second farther side of the cardiac tissue wall (optionally within pericardial cavity 180, as shown in FIG. 8), and the tine-passing portion of the tissue anchor passes between the two tines.

Typically, after the tissue anchor is released from the deployment tool, tension is applied to the tissue anchor by pulling the proximal end of the straight anchor-shaft portion, along the anchor-shaft axis of the straight anchor-shaft portion, away from the tine plane generally defined by the two tines.

For some applications, the tissue anchor is released from the deployment tool such that the intermediate portion is not in mechanical contact with itself or with either of the two tines (either directly, or via a coating or the above-mentioned optional fabric). Pulling the proximal end of the straight anchor-shaft portion away from the tine plane brings the intermediate portion in mechanical contact with at least one element selected from the group consisting of: the intermediate portion and at least one of the two tines. For example, pulling the proximal end of the straight anchor-shaft portion away from the tine plane may bring the intermediate portion in mechanical contact with the tissue-coupling portion at a junction at which the tissue-coupling portion forks into the two tines.

Typically, pulling the proximal end of the straight anchor-shaft portion along the anchor-shaft axis away from the tine plane tightly draws the tines against the second far side of the cardiac tissue wall (typically via visceral pericardium 182).

For some applications, the cardiac tissue wall is a myocardial tissue wall, and the tissue-coupling portion is delivered in the unexpanded generally elongate configuration through the myocardial tissue wall into the pericardial cavity between visceral pericardium and parietal pericardium, generally alongside and against the parietal pericardium, without penetrating the parietal pericardium.

The scope of the present invention includes embodiments described in the following applications, which are assigned to the assignee of the present application and are incorporated herein by reference. For some applications, techniques and apparatus described in one or more of the following applications are combined with techniques and apparatus described herein: U.S. Pat. No. 8,475,525 to Maisano et al.; U.S. Pat. No. 8,961,596 to Maisano et al.; U.S. Pat. No. 8,961,594 to Maisano et al.; PCT Publication WO 2011/089601; U.S. Pat. No. 9,241,702 to Maisano et al.; U.S. Provisional Application 61/750,427, filed Jan. 9, 2013; U.S. Provisional Application 61/783,224, filed Mar. 14, 2013; U.S. Provisional Application 61/897,491, filed Oct. 30, 2013; U.S. Provisional Application 61/897,509, filed Oct. 30, 2013; U.S. Pat. No. 9,307,980 to Gilmore et al.; PCT Publication WO 2014/108903; PCT Publication WO 2014/141239; U.S. Provisional Application 62/014,397, filed Jun. 19, 2014; PCT Publication WO 2015/063580; US Patent Application Publication 2015/0119936; U.S. Provisional Application 62/086,269, filed Dec. 2, 2014; U.S. Provisional Application 62/131,636, filed Mar. 11, 2015; U.S. Provisional Application 62/167,660, filed May 28, 2015; PCT Publication WO 2015/193728; PCT Publication WO 2016/087934; US Patent Application Publication 2016/0235533; US Patent Application Publication 2016/0242762; PCT Publication WO 2016/189391; US Patent Application Publication 2016/0262741; U.S. Provisional Application 62/376,685, filed Aug. 18, 2016; U.S. Provisional Application 62/456,206, filed Feb. 8, 2017; U.S. Provisional Application 62/456,202, filed Feb. 8, 2017; U.S. Provisional Application 62/465,410, filed Mar. 1, 2017; U.S. Provisional Application 62/465,400, filed Mar. 1, 2017; U.S. Provisional Application 62/516,894, filed Jun. 8, 2017; U.S. Provisional Application 62/530,372, filed Jul. 10, 2017; PCT Publication WO 2018/035378; U.S. Provisional Application 62/570,226, filed Oct. 10, 2017; U.S. Provisional Application 62/579,281, filed Oct. 31, 2017; U.S. Provisional Application 62/596,658, filed Dec. 8, 2017; PCT Publication PCT Publication WO 2018/148364; US Patent Application Publication 2018/0221148; U.S. Provisional Application 62/628,457, filed Feb. 9, 2018; PCT Publication WO 2018/160456; US Patent Application Publication 2018/0249993; International Application PCT/US18/036609, filed Jun. 8, 2018; US Patent Application Publication 2018/0353297; PCT Publication WO 2019/013994; International Application PCT/US2018/045523, filed Aug. 7, 2018; PCT Publication WO 2019/074815; PCT Publication WO 2019/089262; and PCT Publication WO 2019/157116.

Patents and patent application publications incorporated by reference in the present patent application are to be considered an integral part of the application except that to the extent any terms are defined in these incorporated patents and patent application publications in a manner that conflicts with the definitions made explicitly or implicitly in the present specification, only the definitions in the present specification should be considered.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A tissue anchor comprising a metal wire that has exactly two wire ends,
wherein the wire is shaped so as to define:
   a straight anchor-shaft portion, and
   a tissue-coupling portion, which extends from a distal end of the straight anchor-shaft portion, such that the straight anchor-shaft portion is disposed along the wire between the tissue-coupling portion and a first of the exactly two wire ends,
wherein the tissue anchor is configured such that when the tissue-coupling portion of the wire is in an unconstrained state in which the tissue-coupling portion is not constrained by any external forces:
   (a) the tissue-coupling portion of the wire is shaped so as to define a tail end portion that includes a second of the exactly two wire ends,
   (b) the tissue-coupling portion of the wire crosses itself at first and second loop-end longitudinal portions along the wire, so as to define a looped portion, which generally defines a looped-portion plane that forms an angle of between 75 and 90 degrees with an anchor-shaft axis of the straight anchor-shaft portion,
   (c) the first loop-end longitudinal portion is closer to the first wire end along the wire than the second loop-end longitudinal portion is to the first wire end along the wire,
   (d) a greatest absolute distance between the first loop-end longitudinal portion and the first wire end is greater than a greatest absolute distance between the second loop-end longitudinal portion and the first wire end, and
   (e) the wire defines only a single looped portion.

2. The tissue anchor according to claim 1, wherein the tissue anchor is configured such that when the tissue-coupling portion of the wire is in the unconstrained state, the anchor-shaft axis does not pass through a space surrounded by and defined by the looped portion.

3. The tissue anchor according to claim 1, wherein the tissue anchor is configured such that when the tissue-coupling portion of the wire is in the unconstrained state, the wire crosses itself exactly once, at the first and the second loop-end longitudinal portions along the wire.

4. The tissue anchor according to claim 1, wherein the wire is not shaped so as to define any looped portions proximal to a proximal end of the straight anchor-shaft portion.

5. The tissue anchor according to claim 1, wherein when the tissue-coupling portion of the wire is in the unconstrained state, the tail end portion generally falls in the looped-portion plane.

6. The tissue anchor according to claim 1, wherein when the tissue-coupling portion of the wire is in the unconstrained state, no portion of the tail end portion is parallel to the straight anchor-shaft portion.

7. The tissue anchor according to claim 1, wherein the tissue anchor is configured such that when the tissue-coupling portion of the wire is in the unconstrained state, the tail end portion is shaped so as to define at least one straight portion.

8. The tissue anchor according to claim 1, wherein a proximal end of the straight anchor-shaft portion is at the first of the exactly two wire ends.

9. The tissue anchor according to claim 1, wherein the tissue anchor is configured such that when the tissue-coupling portion of the wire is in the unconstrained state, the tissue-coupling portion of the wire is shaped so as to define a first-loop-end curved portion along which the first loop-end longitudinal portion is located.

10. The tissue anchor according to claim 9, wherein the tissue anchor is configured such that when a proximal end of the straight anchor-shaft portion is pulled along the anchor-shaft axis away from the looped-portion plane, the wire, at the second loop-end longitudinal portion, snaps into the first loop-end longitudinal portion at the first-loop-end curved portion of the wire.

11. The tissue anchor according to claim 1, wherein the tissue anchor is configured such that when the tissue-coupling portion of the wire is in the unconstrained state, the looped portion includes exactly one turn.

* * * * *